United States Patent
Takahashi et al.

(10) Patent No.: US 10,168,314 B2
(45) Date of Patent: Jan. 1, 2019

(54) LIVE CELL ANALYSIS APPARATUS, METHOD FOR ANALYZING LIVE CELLS, SYSTEM FOR ANALYZING LIVE CELLS AND NON-TRANSITORY DATA STORAGE MEDIUM

(71) Applicant: SONY CORPORATION, Tokyo (JP)

(72) Inventors: Kazuya Takahashi, Tokyo (JP); Tomohiro Hayakawa, Saitama (JP); Hirokazu Tatsuta, Kanagawa (JP); Eriko Matsui, Tokyo (JP)

(73) Assignee: SONY CORPORATION, Tokyo (JP)

( * ) Notice: Subject to any disclaimer, the term of this patent is extended or adjusted under 35 U.S.C. 154(b) by 109 days.

(21) Appl. No.: 15/119,684

(22) PCT Filed: Feb. 13, 2015

(86) PCT No.: PCT/JP2015/000660
§ 371 (c)(1),
(2) Date: Aug. 17, 2016

(87) PCT Pub. No.: WO2015/133069
PCT Pub. Date: Sep. 11, 2015

(65) Prior Publication Data
US 2017/0010253 A1    Jan. 12, 2017

(30) Foreign Application Priority Data

Mar. 3, 2014  (JP) .................. 2014-040577
Dec. 10, 2014 (JP) .................. 2014-249668

(51) Int. Cl.
G01N 33/487     (2006.01)

(52) U.S. Cl.
CPC . *G01N 33/48792* (2013.01); *G01N 33/48707* (2013.01); *G01N 33/48728* (2013.01)

(58) Field of Classification Search
CPC ....... G01N 33/48707; G01N 33/48728; G01N 33/48792; G06T 2207/30004
See application file for complete search history.

(56) References Cited

U.S. PATENT DOCUMENTS 5,639,614 A * 6/1997 Sen ............... C07K 14/705
435/6.17
2004/0009566 A1 * 1/2004 Okano ............ A61L 27/3826
435/174

(Continued)

FOREIGN PATENT DOCUMENTS

JP    2013-021961 A    2/2013
JP    2013-094168 A    5/2013

(Continued)

OTHER PUBLICATIONS

Bazan et al. "Image Processing Techniques for Assessing Contractility in Isolated Adult Cardiac Myocytes." International Journal of Biomedical Imaging, vol. 2009, Article ID 352954, Nov. 2009, pp. 1-11.*

(Continued)

*Primary Examiner* — Jon Chang
(74) *Attorney, Agent, or Firm* — Chip Law Group

(57) ABSTRACT

Described are methods and structures associated with live cell analysis apparatus. A live cell analysis apparatus may include at least one data processor that is configured to process a sequence of images of live cells to determine motion of one or more live cells. The motion may be in response to applied electrical stimulations. The apparatus and methods may be used to determine a refractory period for cardiomyocytes from the determined motion.

21 Claims, 20 Drawing Sheets

(56) References Cited

U.S. PATENT DOCUMENTS

| | | | |
|---|---|---|---|
| 2013/0041265 A1* | 2/2013 | Sostek | A61B 17/3478 600/473 |
| 2014/0203818 A1* | 7/2014 | Wang | G01N 27/02 324/603 |

FOREIGN PATENT DOCUMENTS

| | | |
|---|---|---|
| WO | 2010/004365 A1 | 1/2010 |
| WO | 2013/086512 A2 | 6/2013 |

OTHER PUBLICATIONS

Steadman et al. "A Video System for Measuring Motion in Contracting Heart Cells." IEEE Transactions on Biomedical Engineering, vol. 35, No. 4, Apr. 1988, pp. 264-272.*

Mukherjee et al. "Measurement of Dynamic Cellular and Sarcomere Contractile Properties from the Same Cardiocyte." 14th Annual International Conference of the IEEE Engineering in Medicine and Biology Society, Oct. 29, 1992, pp. 392-393.*

Hayakawa et al. "Noninvasive Evaluation of Contractile Behavior of Cardiomyocyte Monolayers Based on Motion Vector Analysis." Tissue Engineering, Part C, vol. 18, No. 1, Oct. 3, 2011, pp. 21-32.*

David J. Chariot, "Automation in Image Cytometry : Continuous Hcs and Kinetic Image Cytometry", UC San Diego Electronic Theses and Dissertations, Bioengineering, Available Online at http://escholarship.org/uc/item/4303h3x1, 2012, 122 pages.

Tandon, et al., "Electrical Stimulation Systems for Cardiac Tissue Engineering", Nature Protocols, vol. 4, No. 2, Jan. 22, 2009, pp. 155-173.

Tandon, et al., "Surface-Patterned Electrode Bioreactor for Electrical Stimulation", Lab Chip., vol. 10, No. 6, Mar. 21, 2010, pp. 692-700.

"Imaging Software NIS-Elements", Nikon, Sep. 2008, pp. 07.

Nina Tandon et al., "Electrical stimulation systems for cardiac tissue engineering", Protocol, Nature Protocols, vol. 4, No. 2, Published online Jan. 22, 2009, doi:10.1038/nprot.2008.183, 2009, pp. 19.

David J. Charlot, "Automation in image cytometry : continuous HCS and kinetic image cytometry", UC San Diego Electronic Theses and Dissertations, eScholarship University of California, 2012, pp. 122.

Nina Tandon et al., "Surface-patterned electrode bioreactor for electrical stimulation", Paper, Lab on a Chip, DOI: 10.1039/b917743d, Received Sep. 3, 2009, Accepted Nov. 27, 2009 First published as an Advance Article on the web Jan. 5, 2010, The Royal Society of Chemistry, 2010, pp. 9.

Nikon, "NIS Elements", Advanced Solutions for your Imaging World, Imaging Software, Japan, 2008, pp. 7.

* cited by examiner

[Fig. 1]
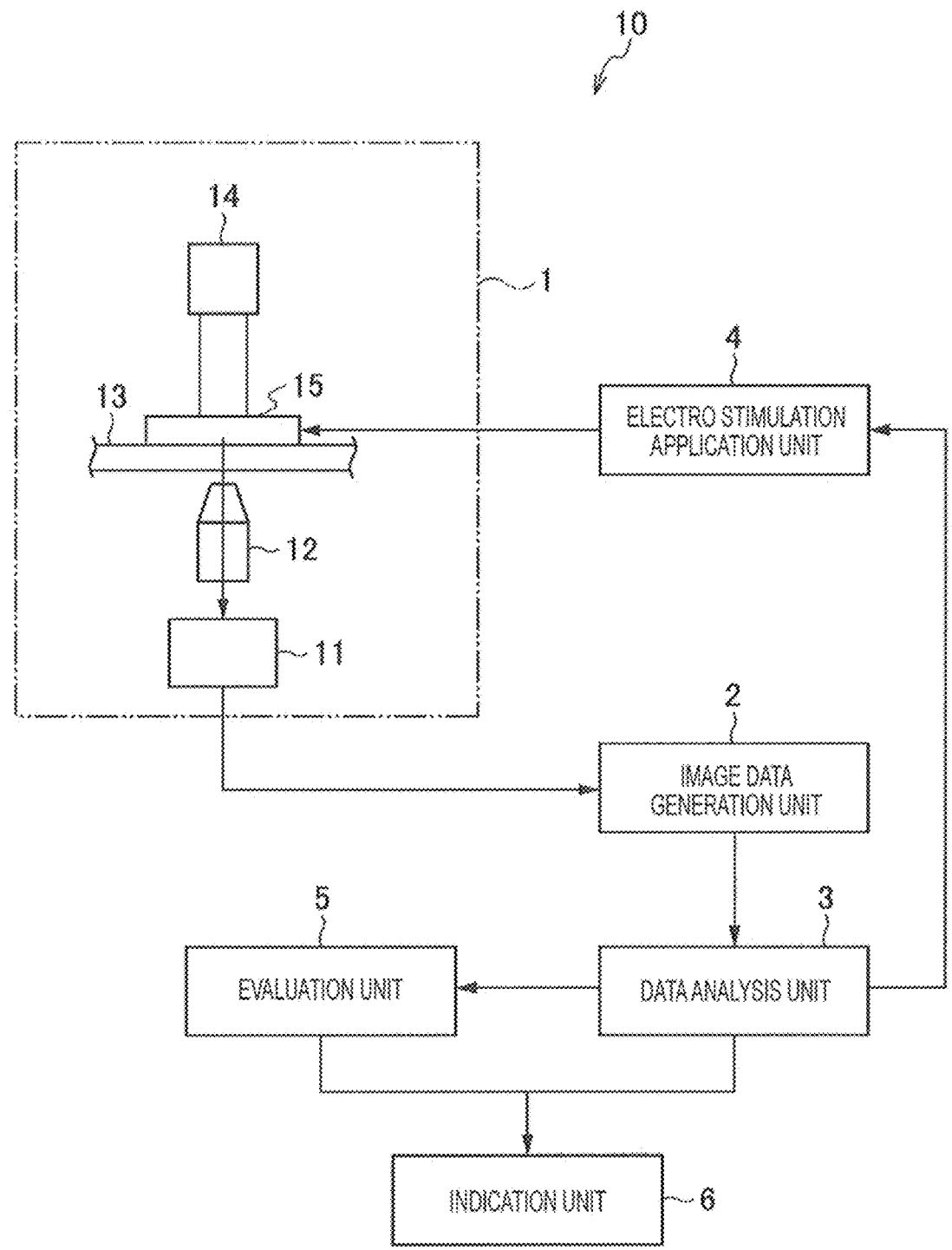

[Fig. 2]
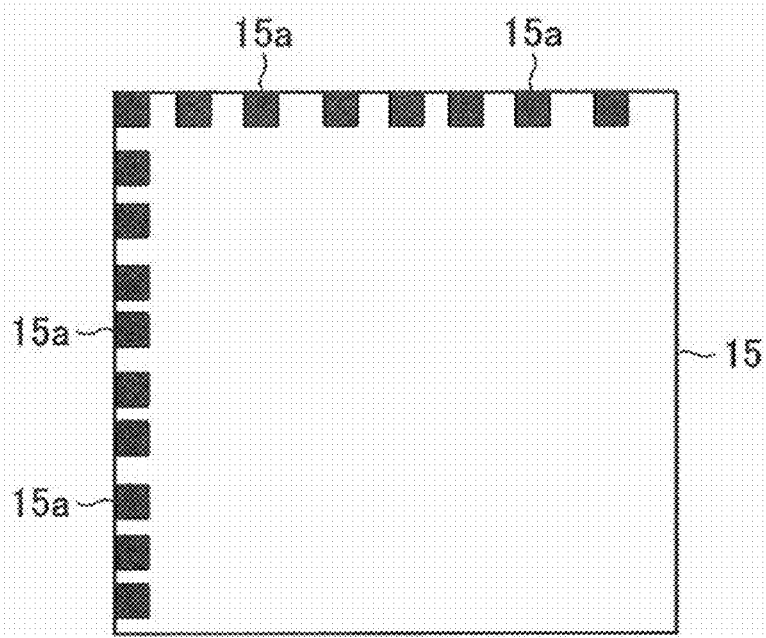
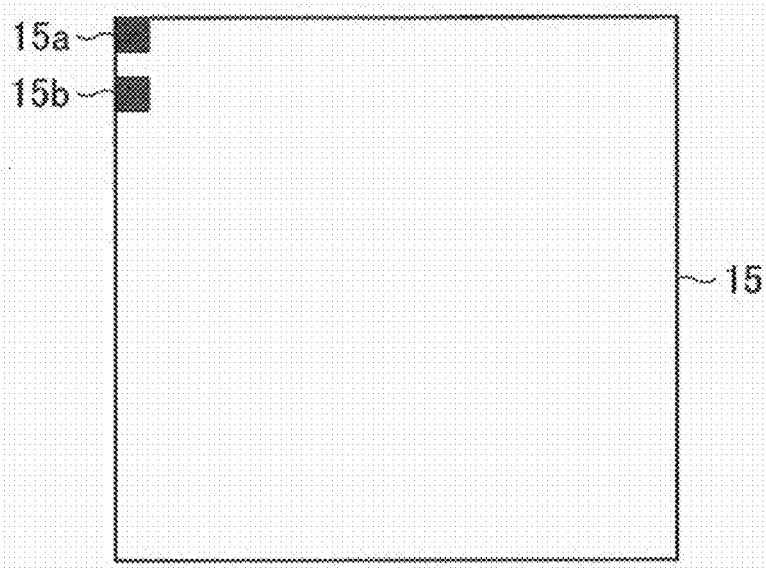

[Fig. 3]
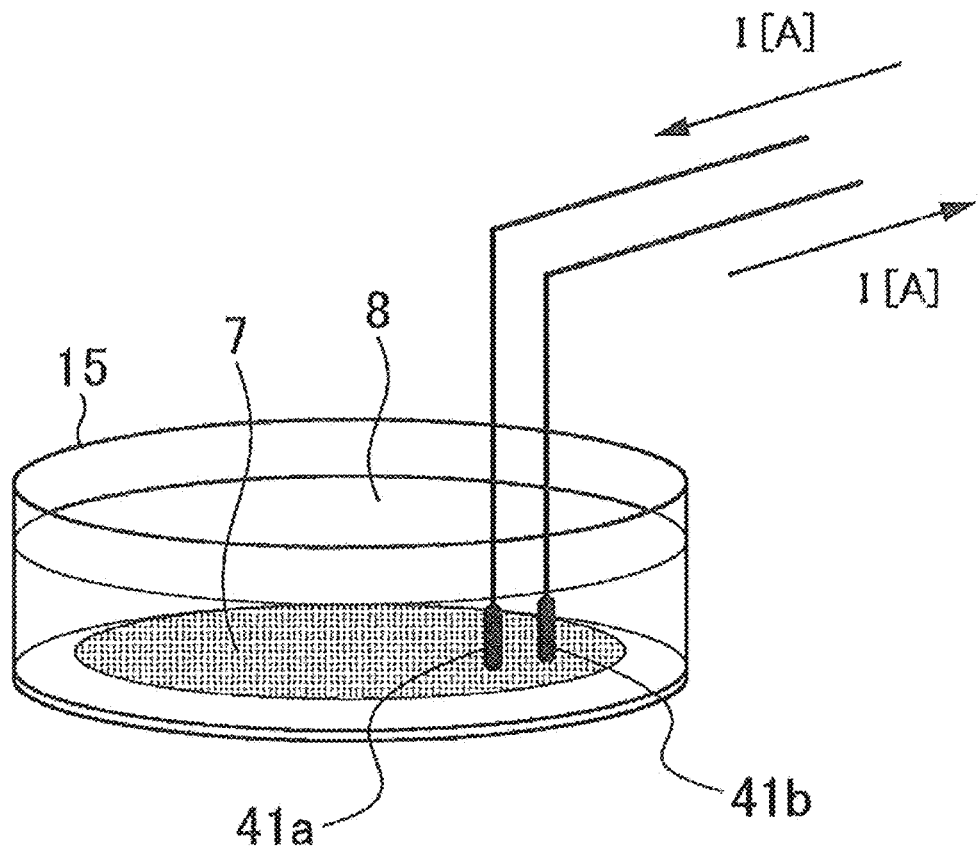
[Fig. 4]
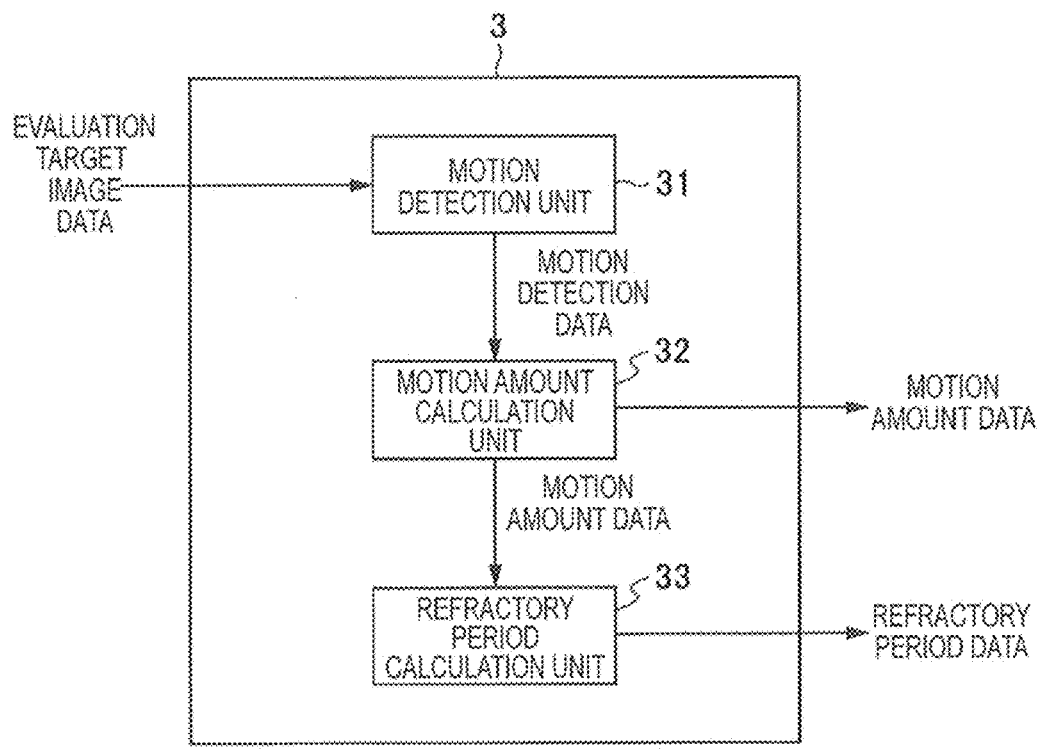

[Fig. 5]
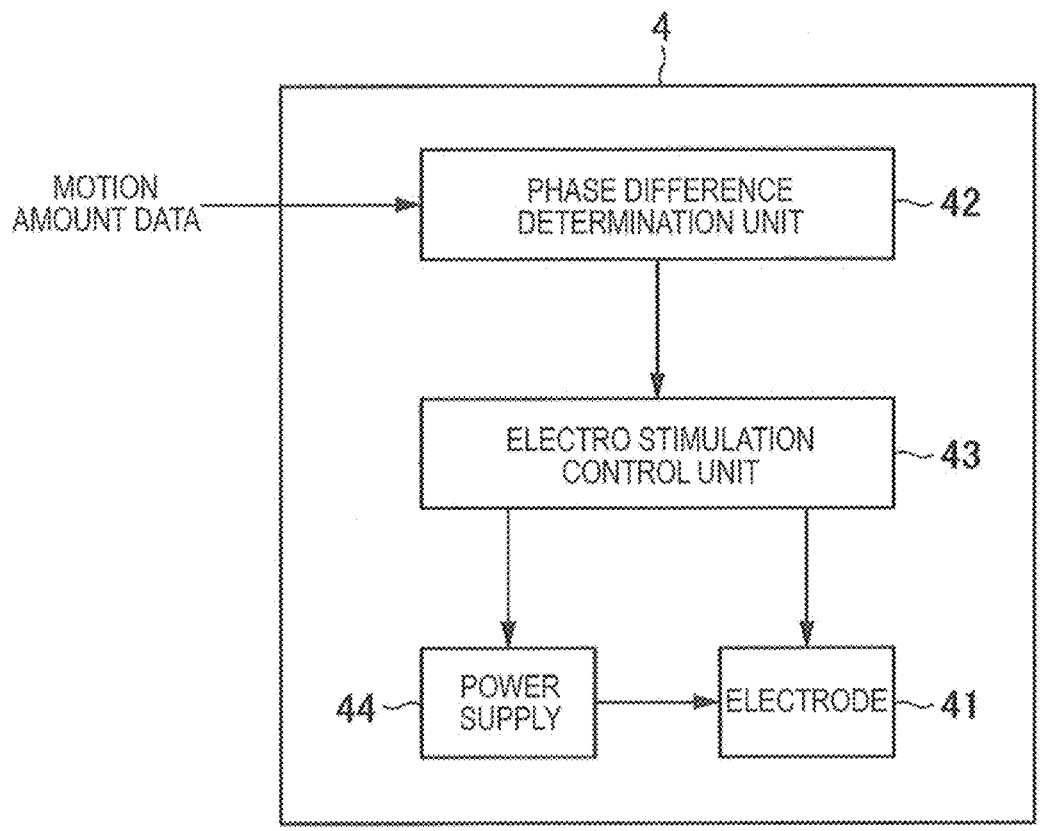

[Fig. 6]
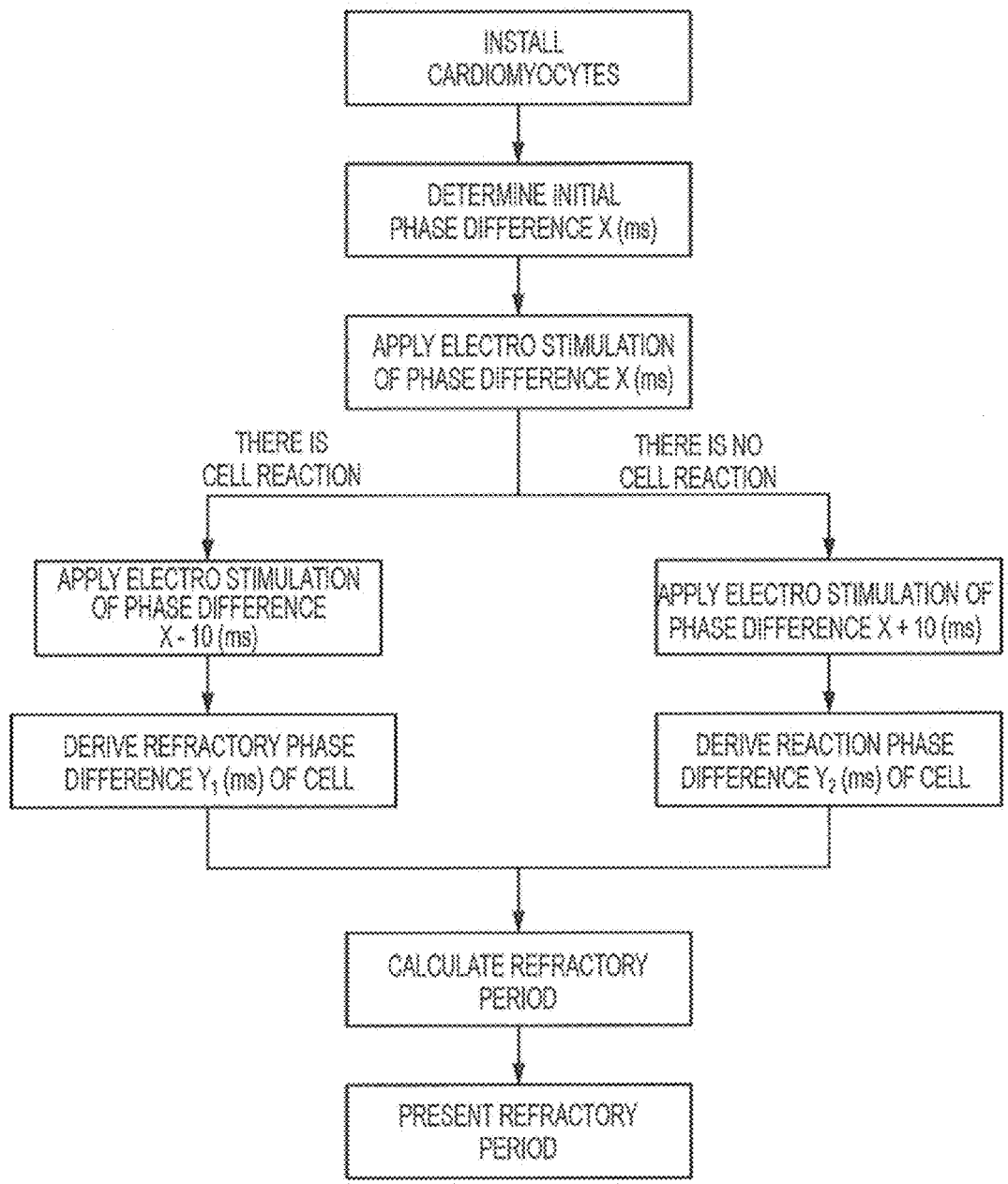

[Fig. 7]
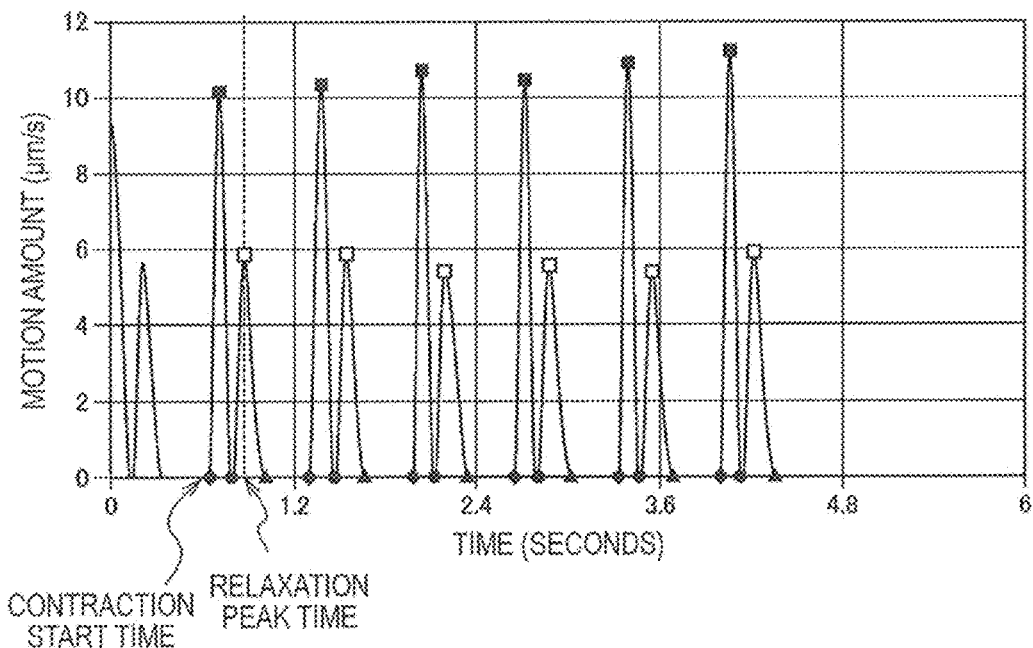
[Fig. 8]
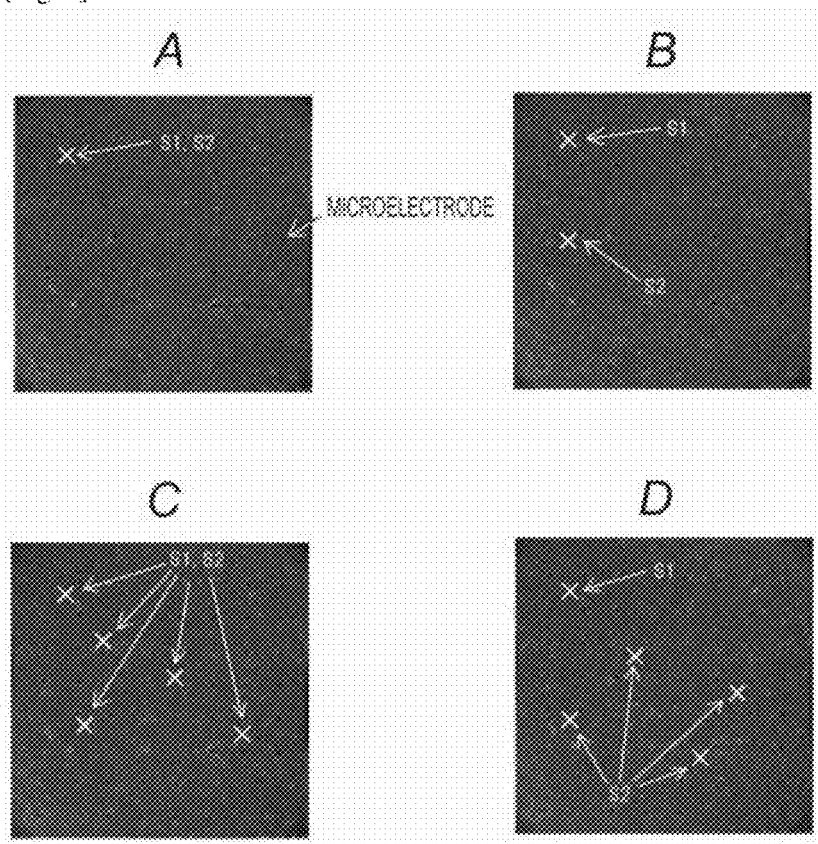

[Fig. 9]
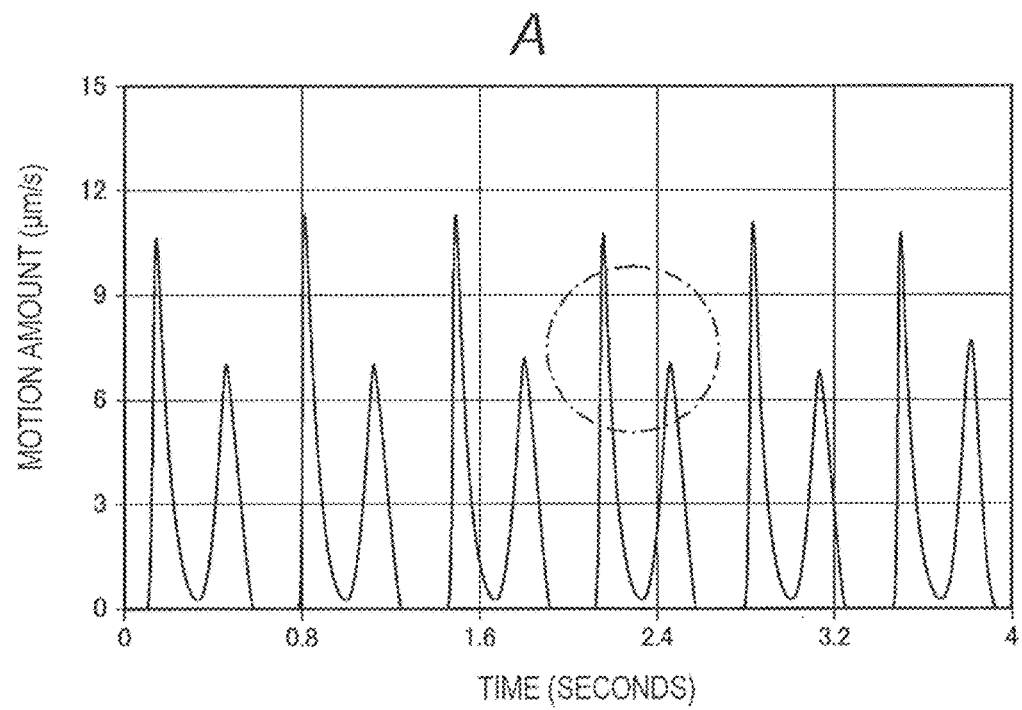
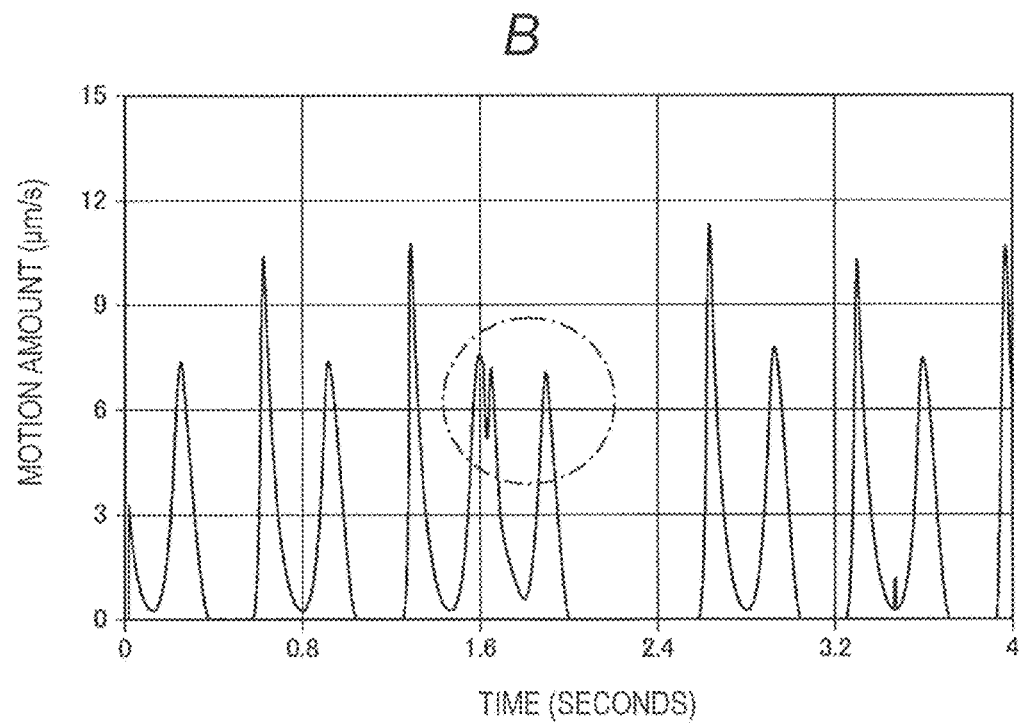

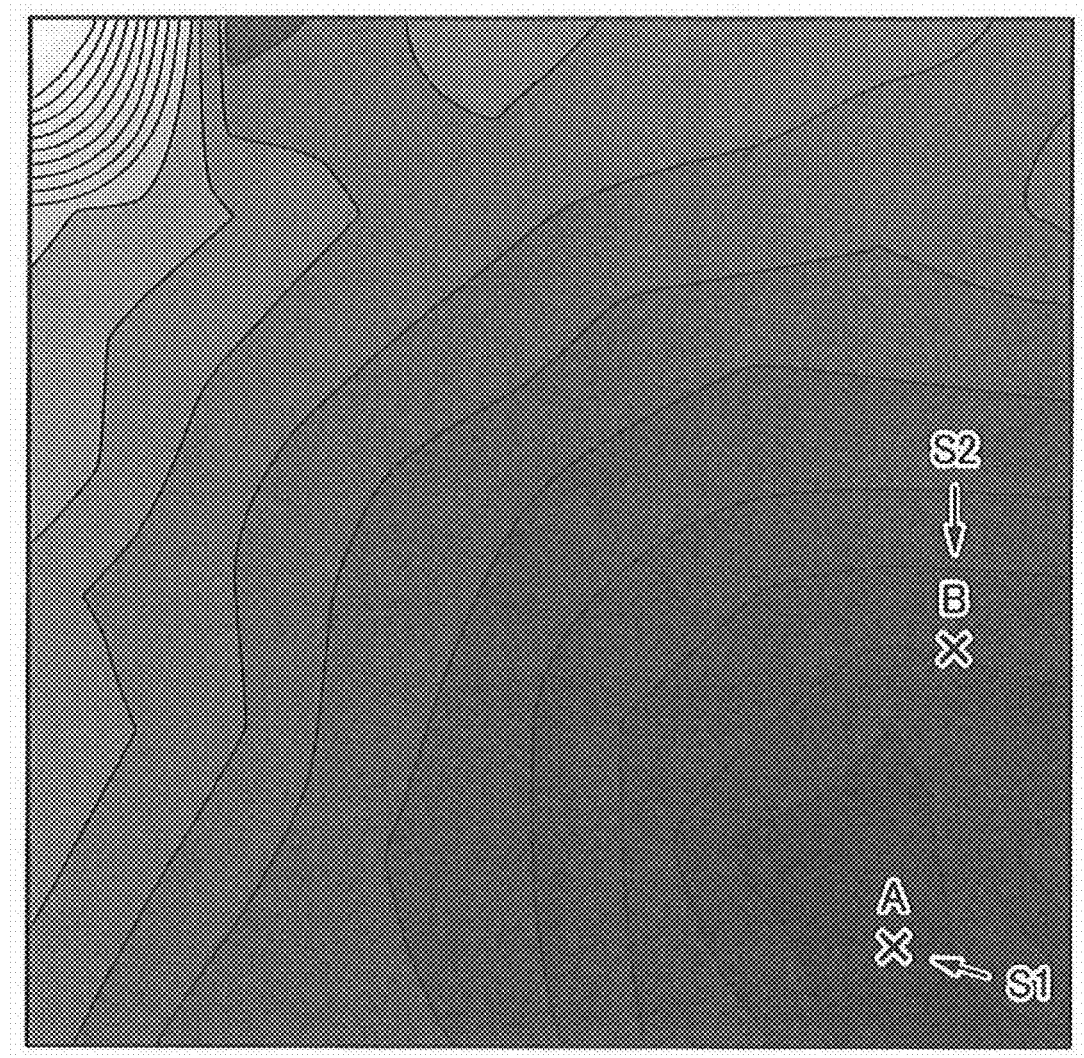
[Fig. 10]

[Fig. 11]
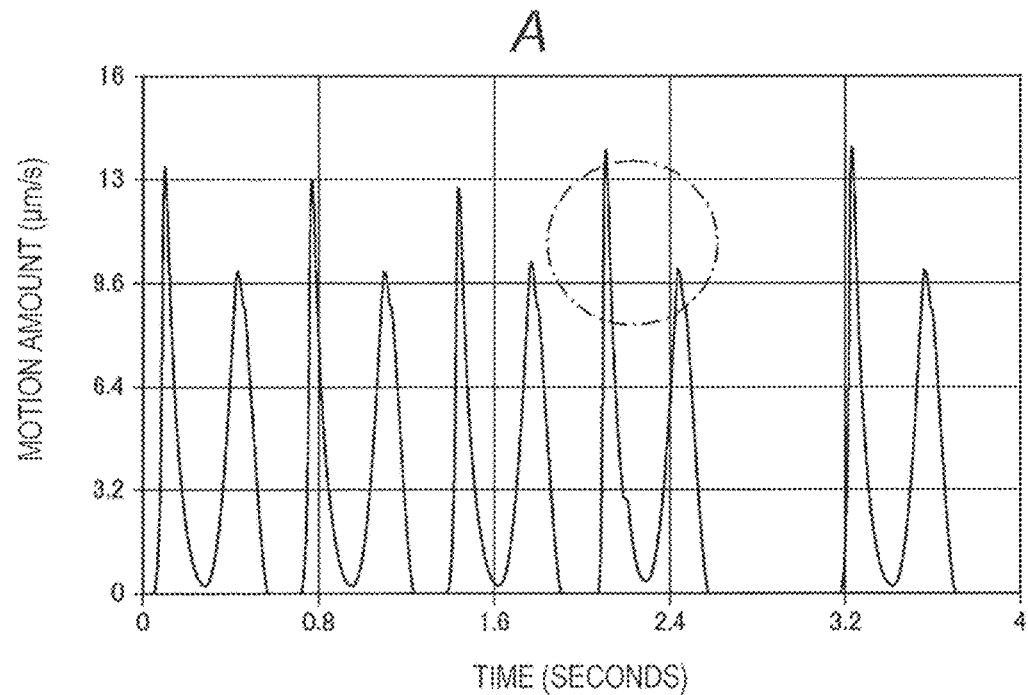
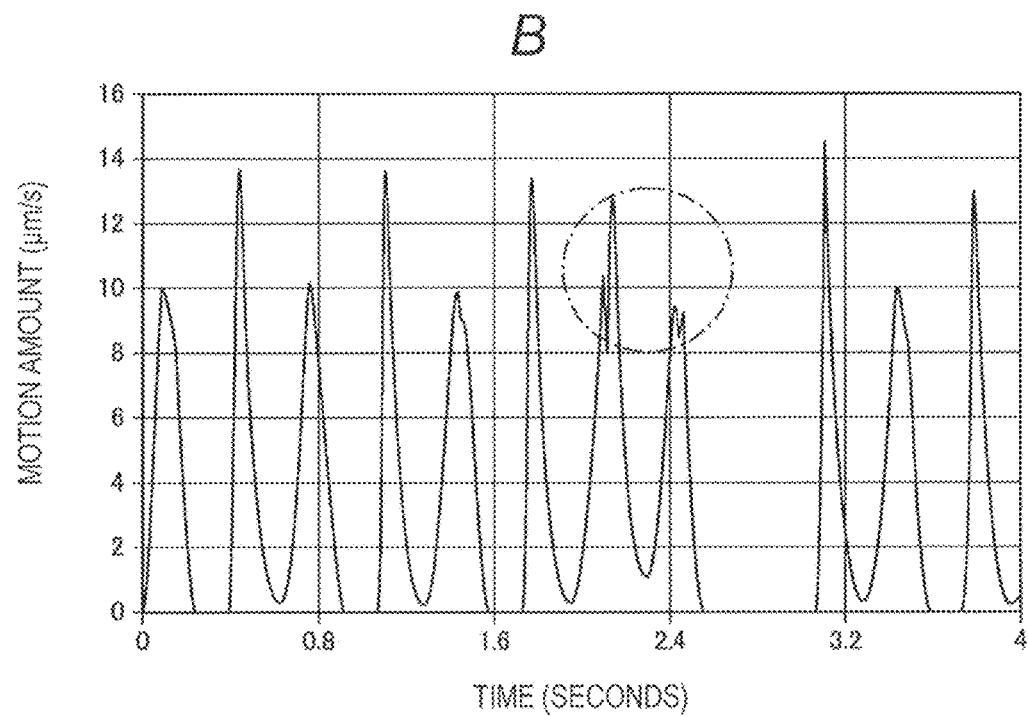

[Fig. 12]
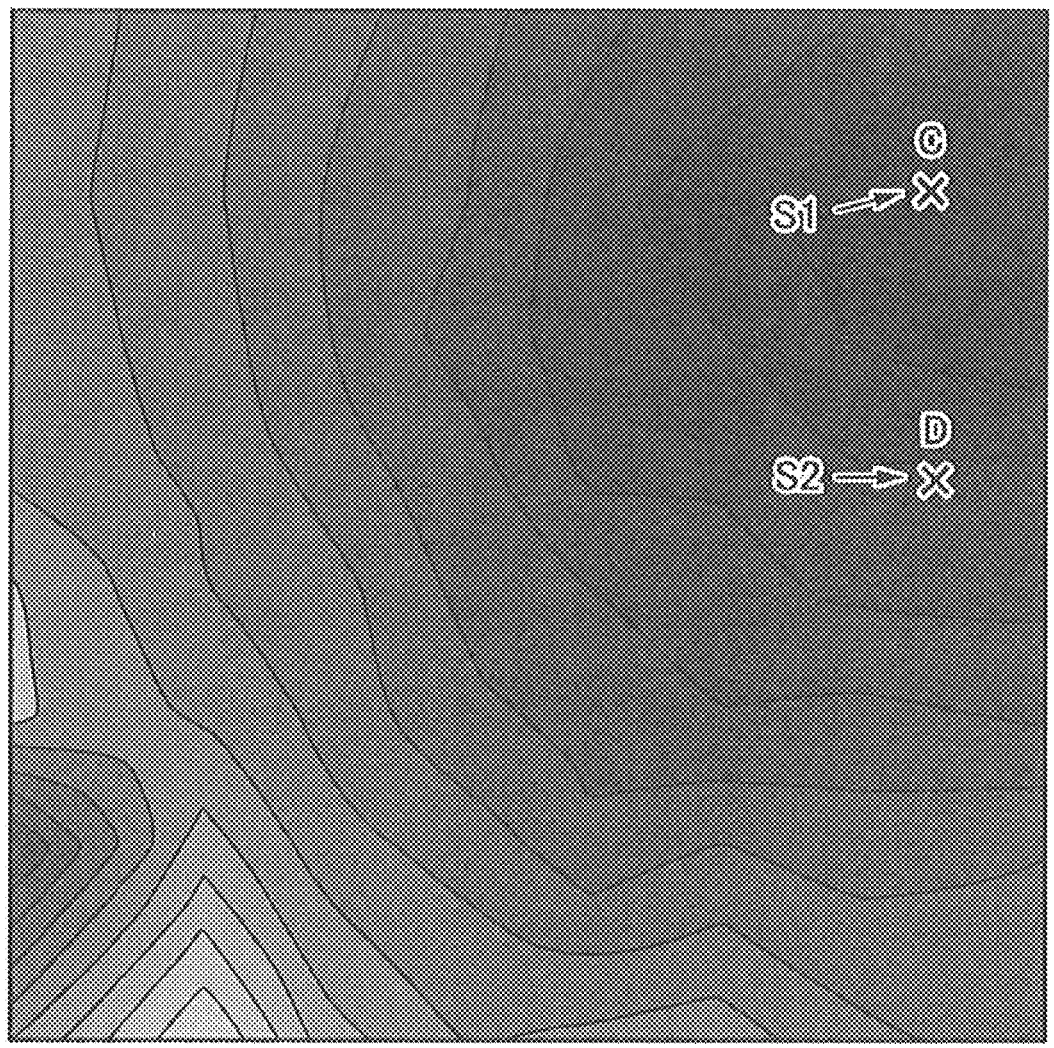

[Fig. 13]
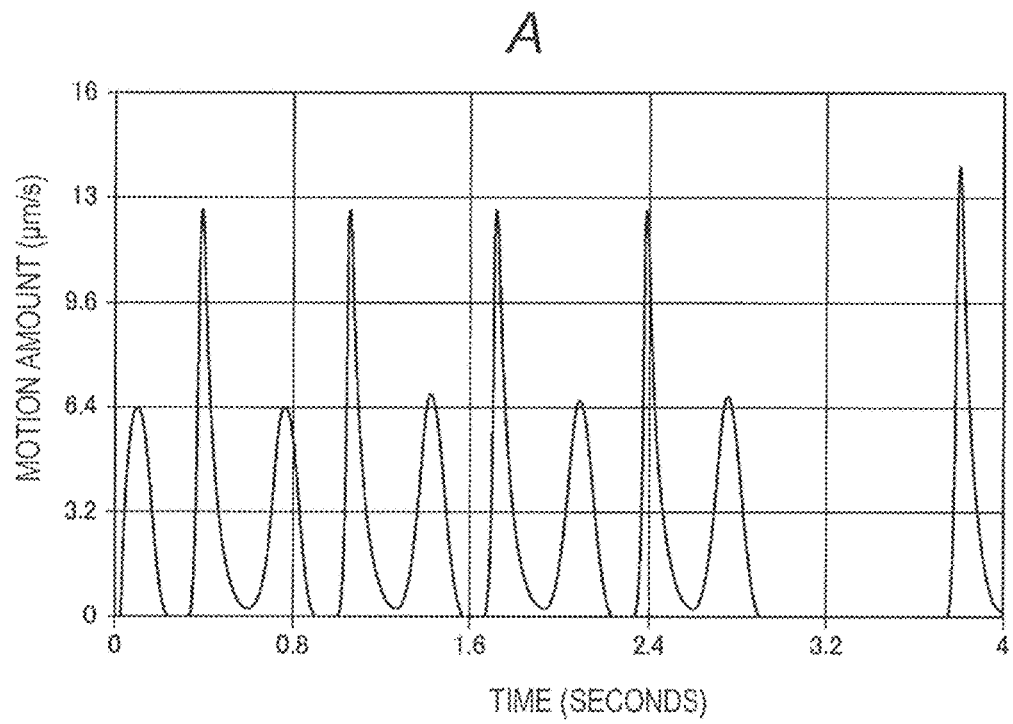
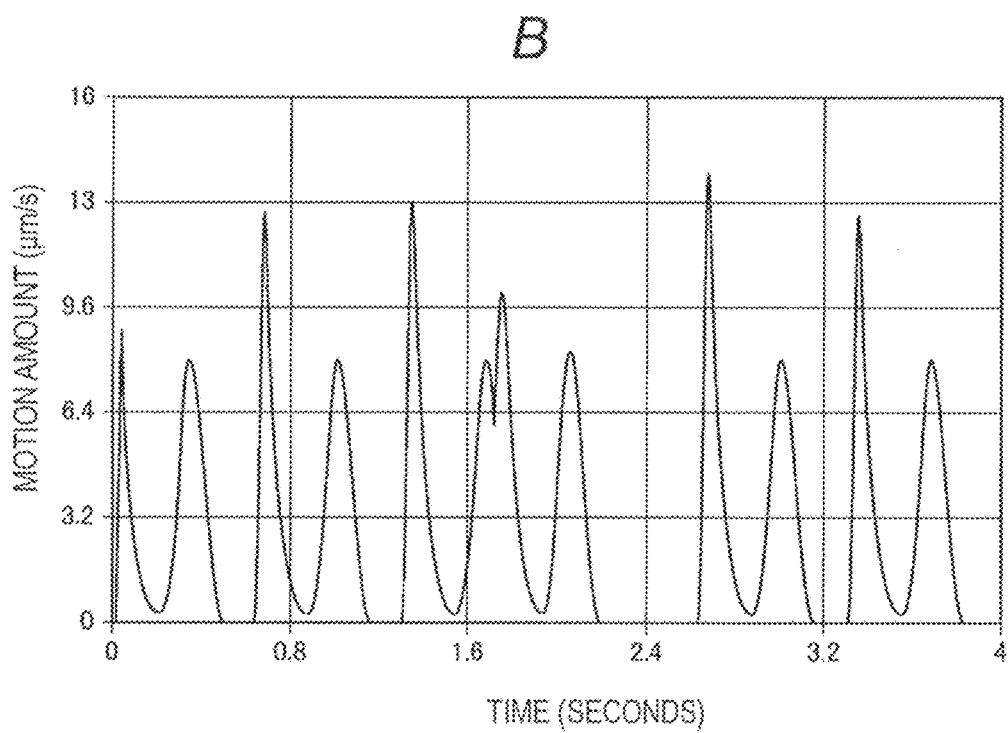

[Fig. 14]
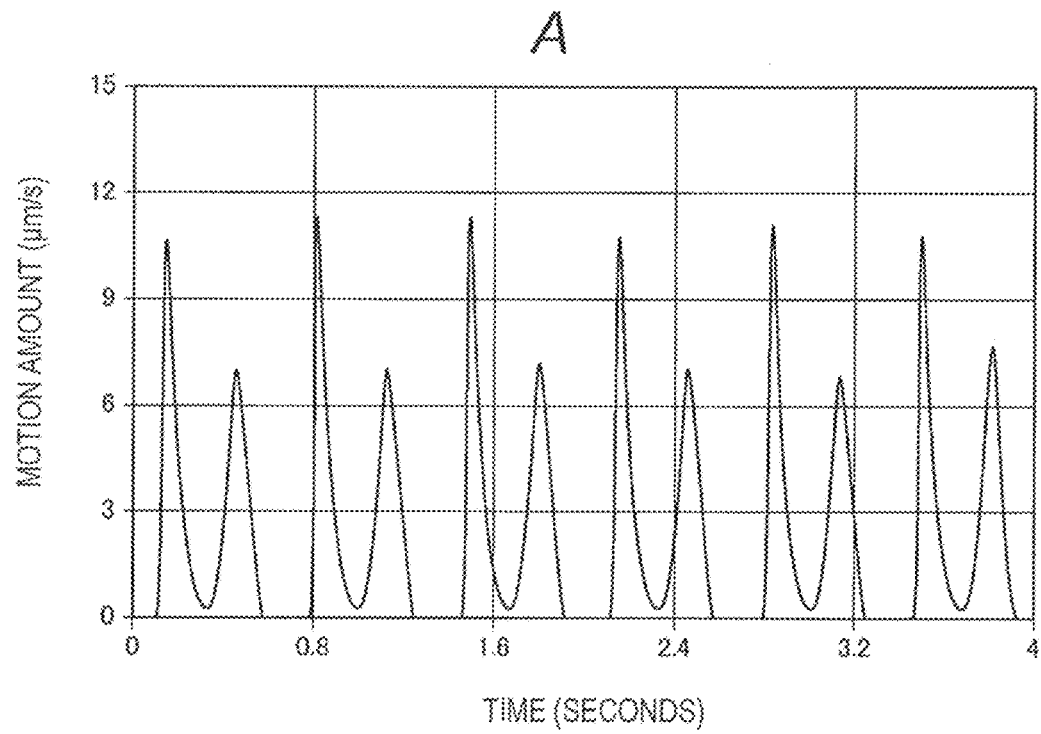
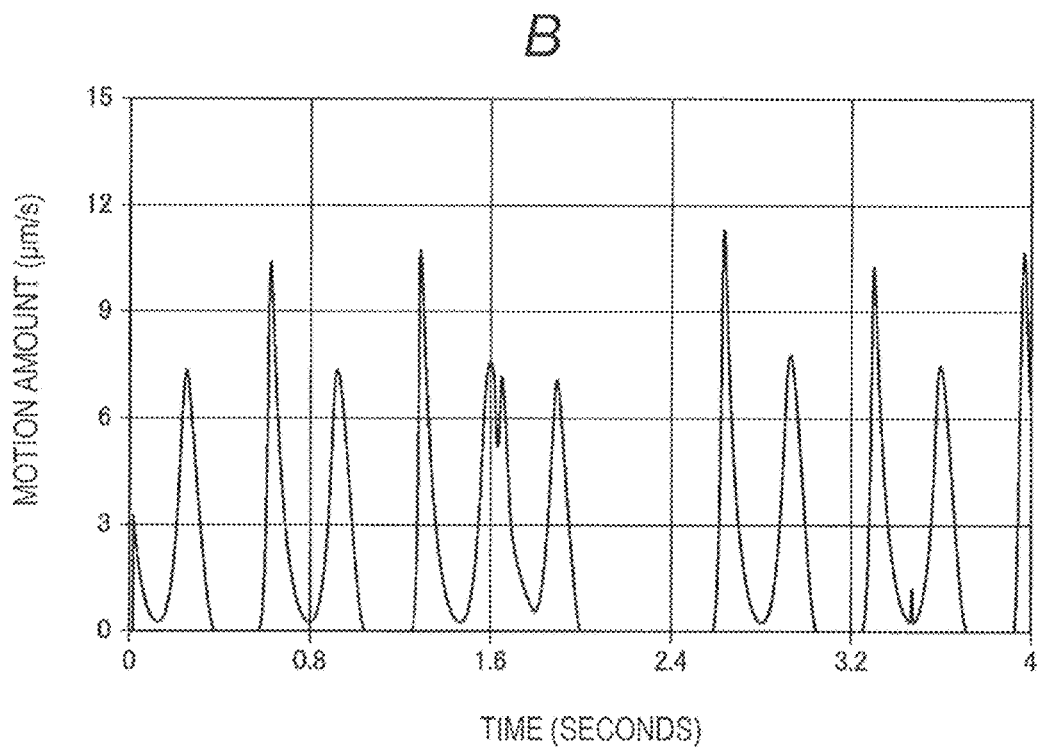

[Fig. 15]
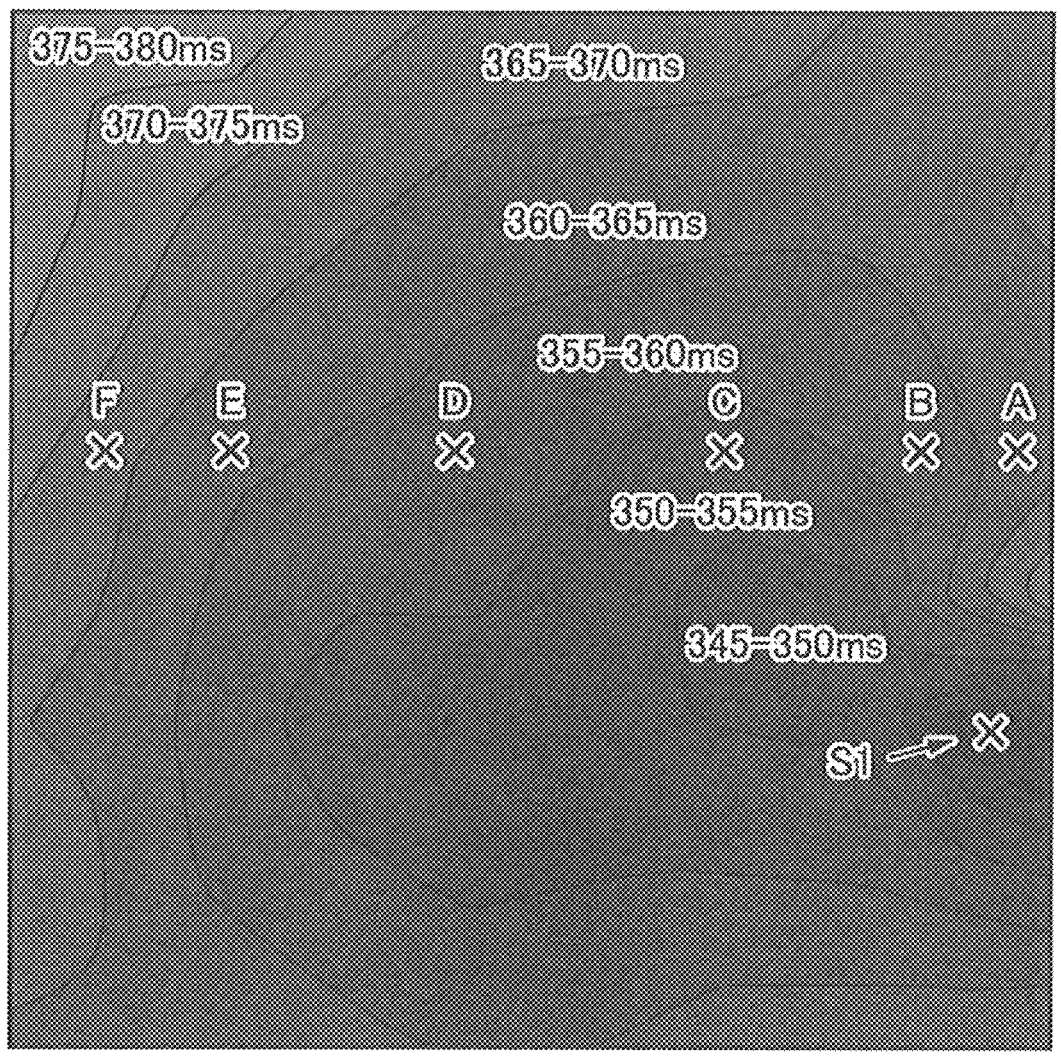

[Fig. 16]
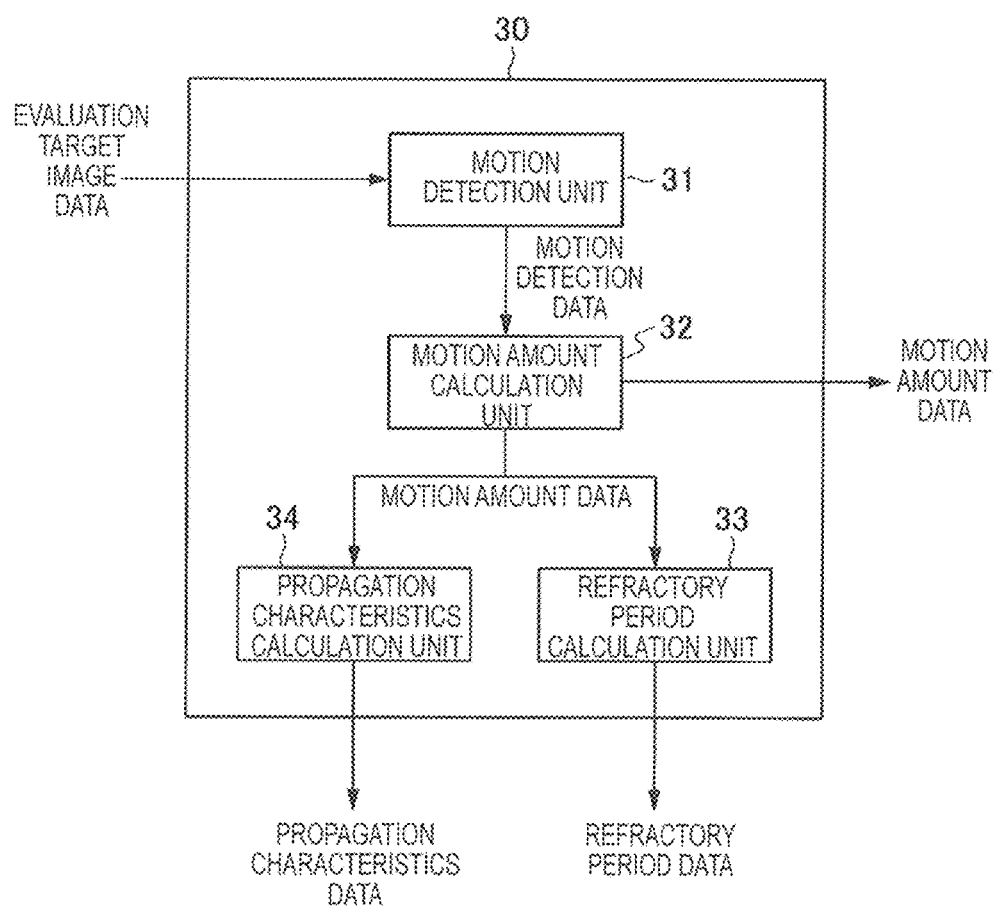

[Fig. 17]
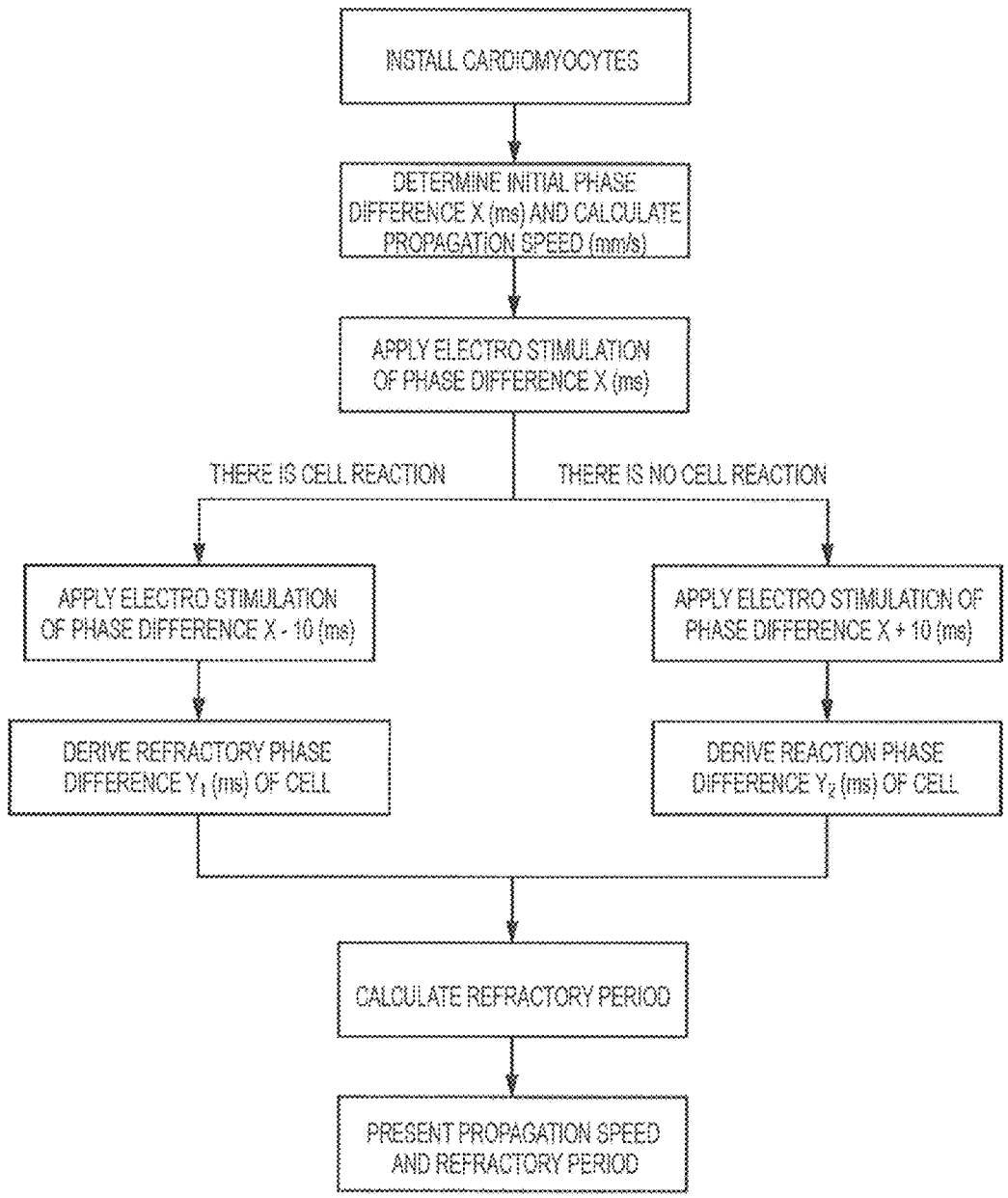

[Fig. 18]
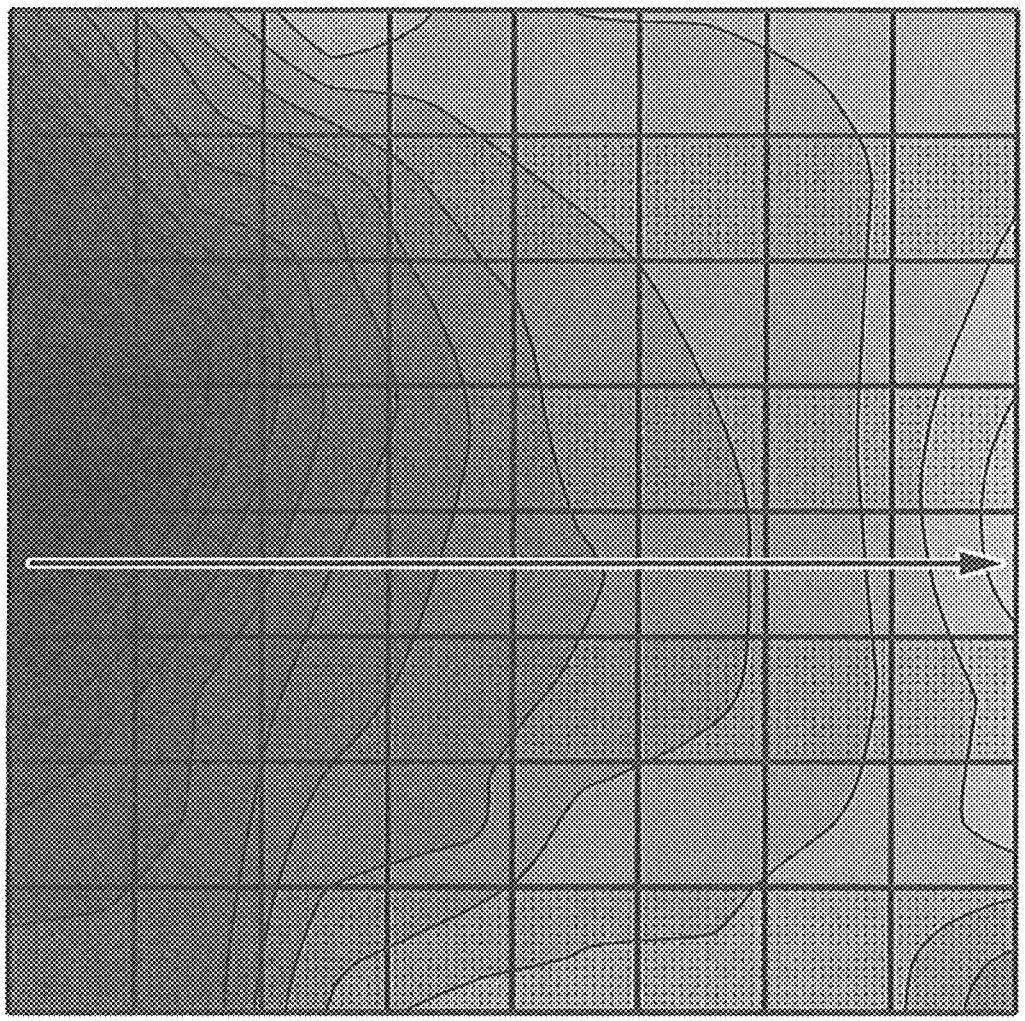

[Fig. 19]
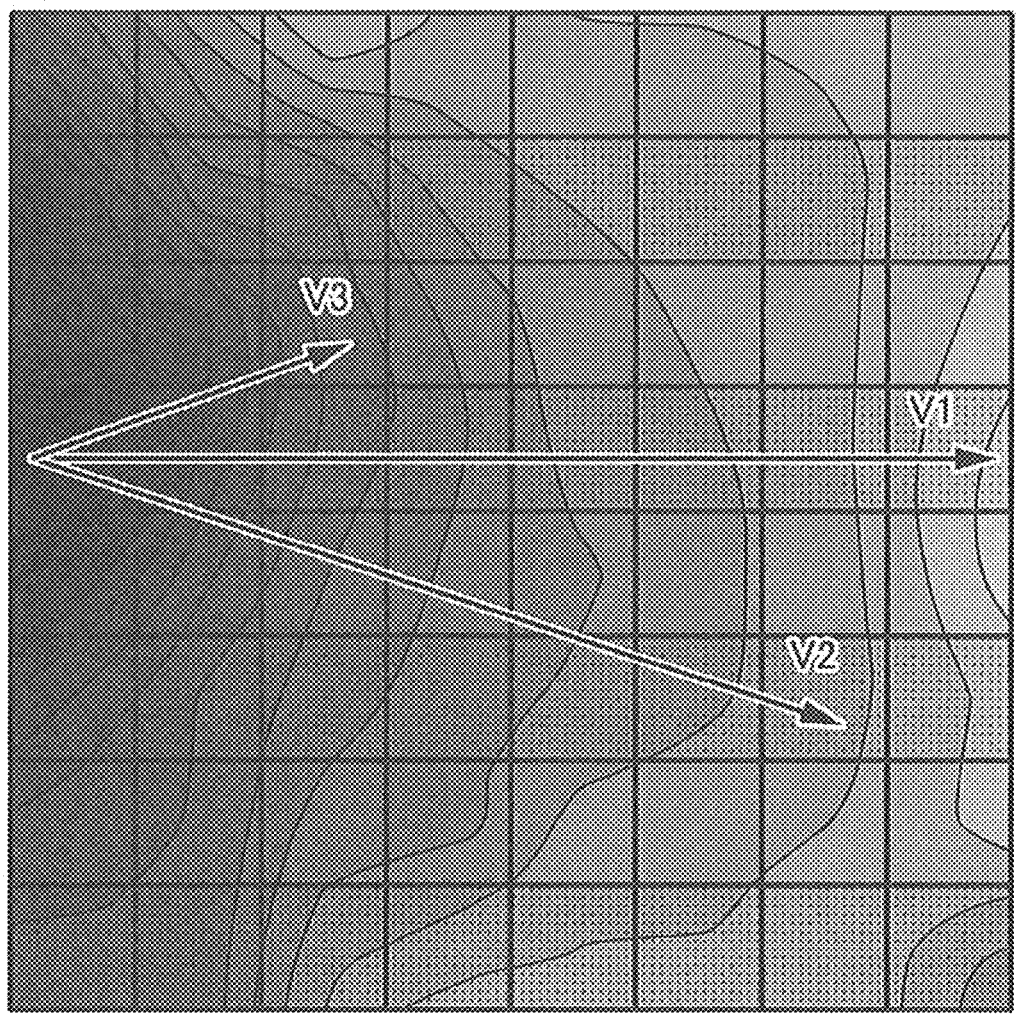

[Fig. 20]
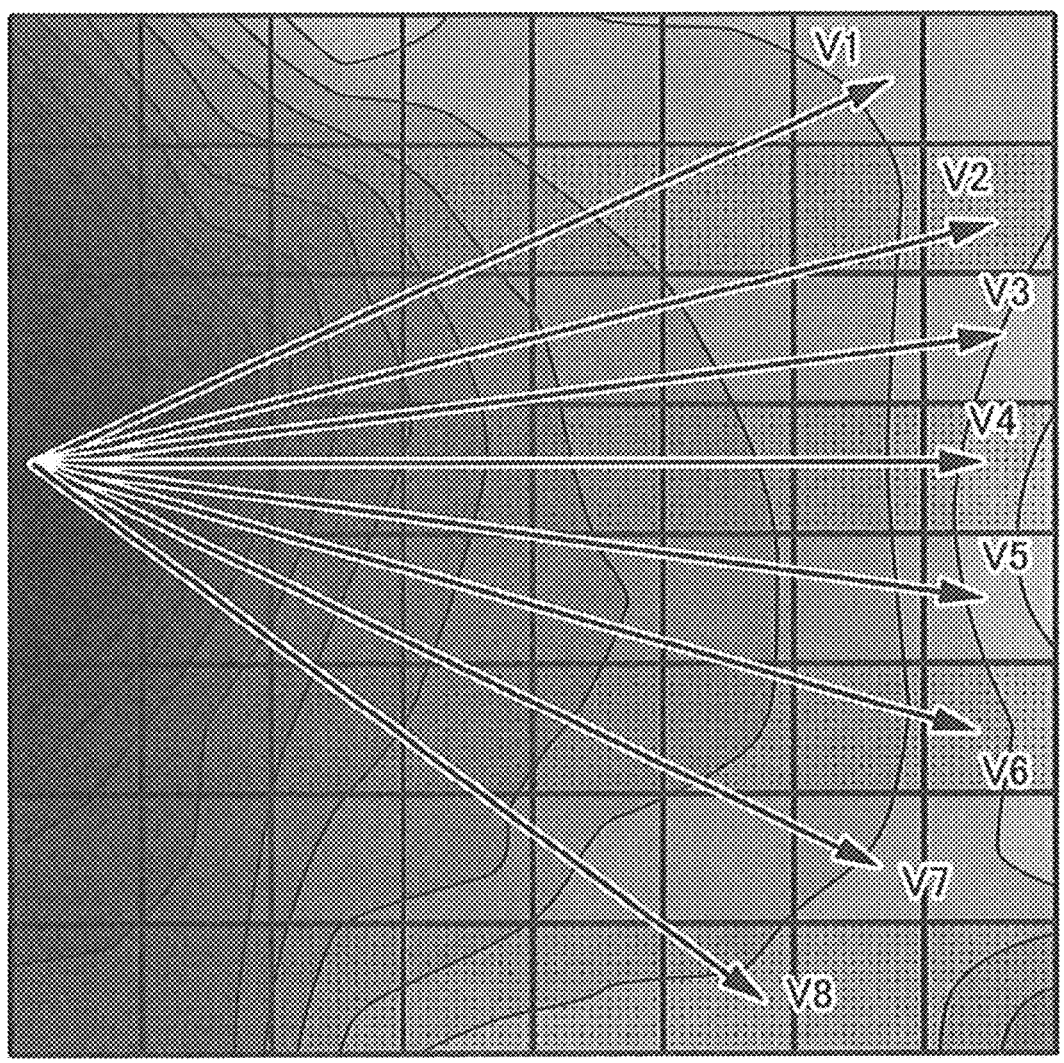

[Fig. 21]
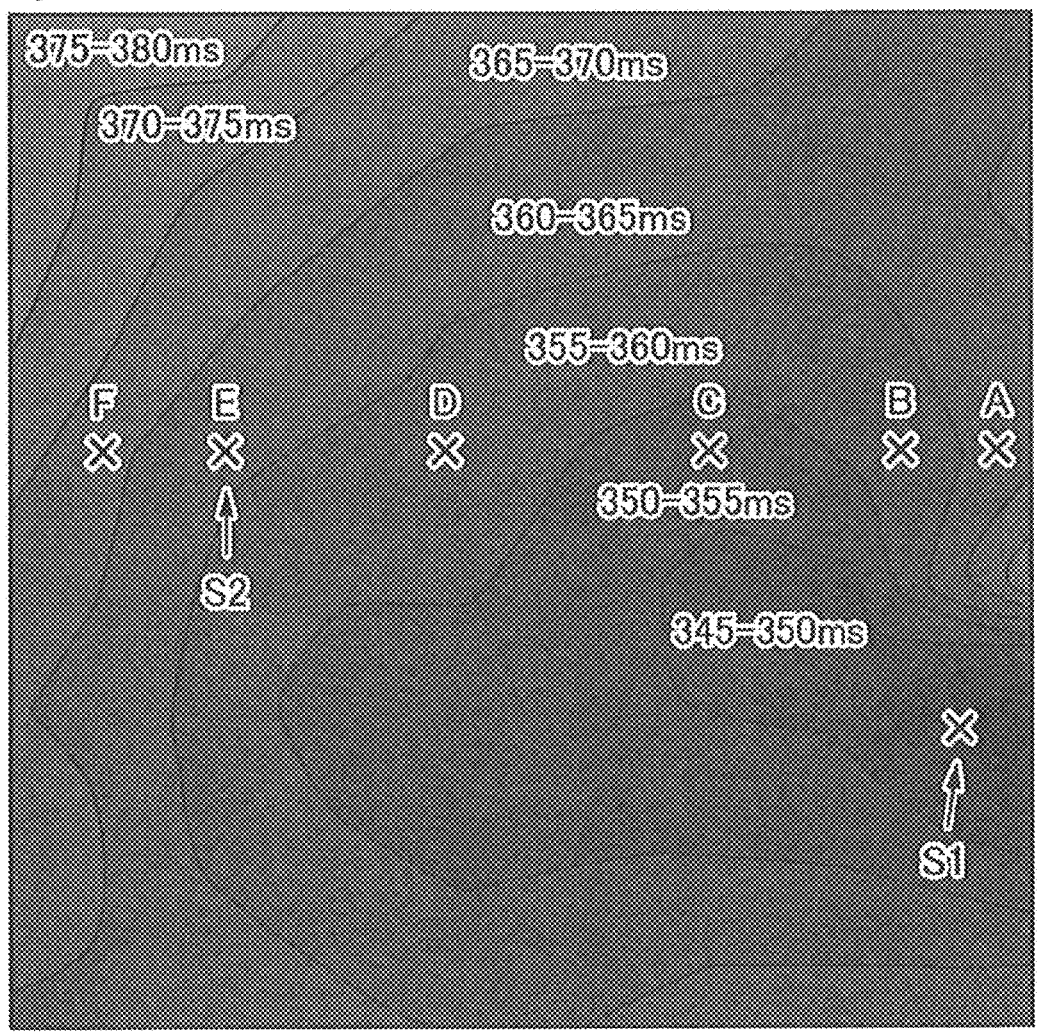

[Fig. 22]
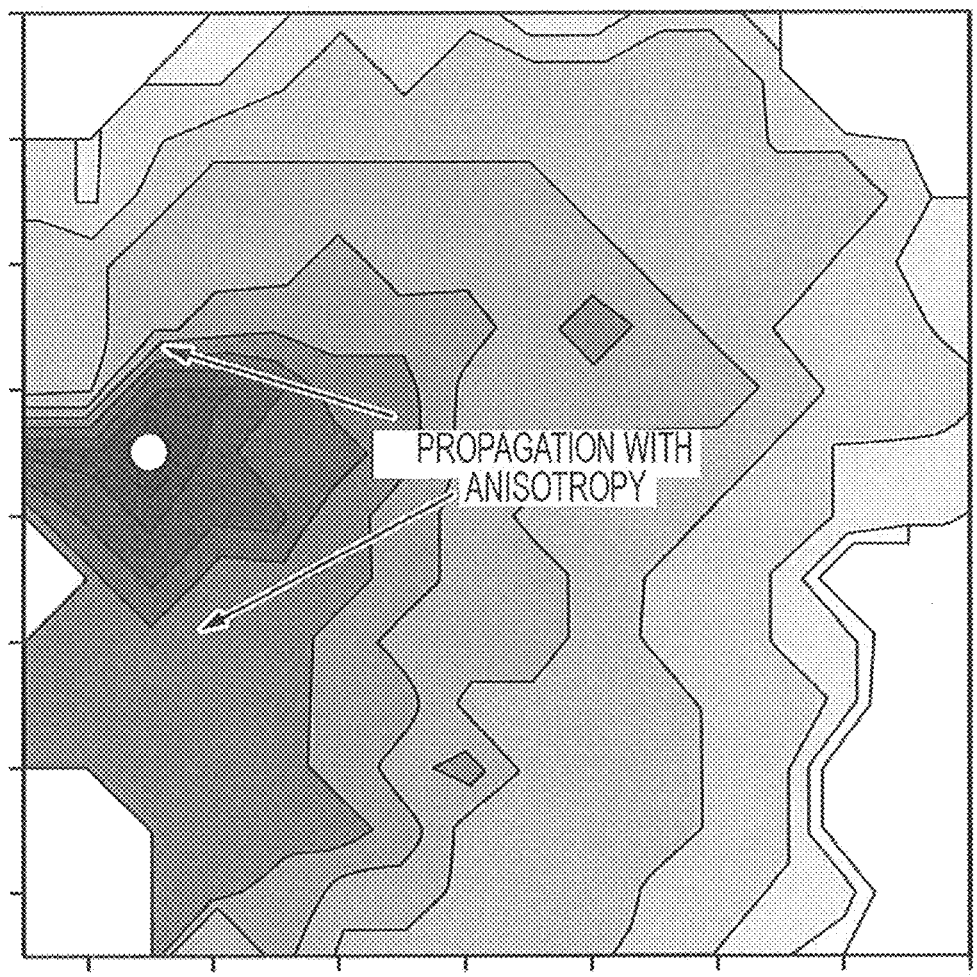
[Fig. 23]
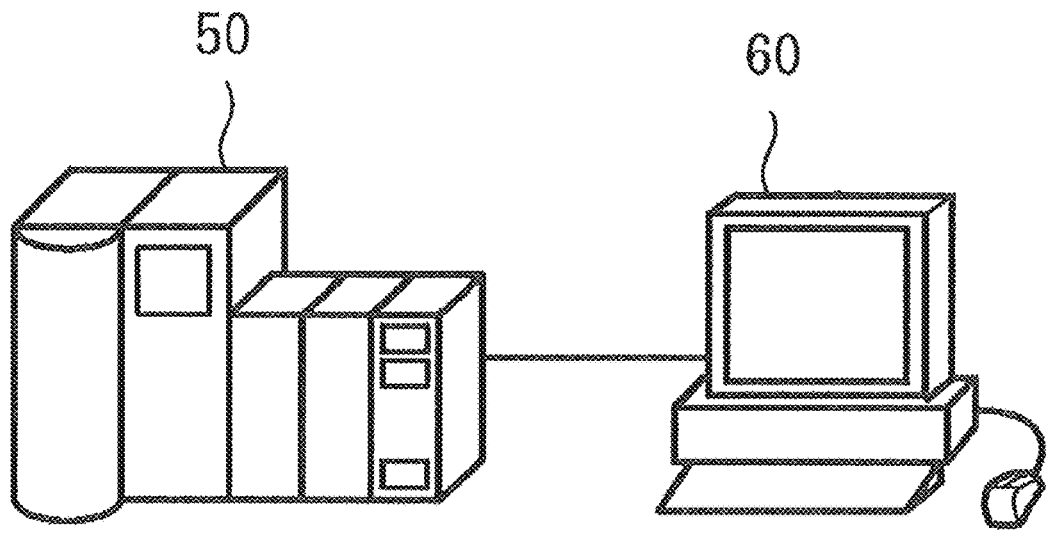

LIVE CELL ANALYSIS APPARATUS, METHOD FOR ANALYZING LIVE CELLS, SYSTEM FOR ANALYZING LIVE CELLS AND NON-TRANSITORY DATA STORAGE MEDIUM

CROSS REFERENCE TO RELATED APPLICATIONS

This application is a U.S. National Phase of International Patent Application No. PCT/JP2015/000660 filed on Feb. 13, 2015, which claims priority benefit of Japanese Patent Application No. 2014-040577 filed in the Japan Patent Office on Mar. 3, 2014 and of Japanese Patent Application No. 2014-249668 filed in the Japan Patent Office on Dec. 10, 2014. Each of the above-referenced applications is hereby incorporated herein by reference in its entirety.

TECHNICAL FIELD

The present technique relates to a cell evaluation apparatus, a cell evaluation method, a data analysis apparatus, and a data analysis method. More particularly, the present technique relates to a technique of evaluating the state and characteristics of cardiomyocytes.

BACKGROUND ART

In recent years, a technique has been developed to evaluate the effect and the safety in the development of new pharmaceuticals and model tests of cardiac diseases such as arrhythmia by using cardiomyocytes and cardiomyocytes sheets made according to cell culturing technique. In particular, the cardiac toxicity test for evaluating toxicity and side effects on the heart and cardiac muscles is required to be carried out for all of the drugs, and the nonclinical test method using culturing cells is expected to be used as an alternative method replacing test methods involving animal experiments.

Examples of cardiomyocytes evaluation methods include an electrode array (micro electrode arrays: MEA) method (see, for example, PTL 1) and a method using image processing technique such as a calcium imaging method (see, for example, PTL 2). The MEA method is a method of performing evaluation by making use of the fact that the contraction and relaxation motions of cardiomyocytes are controlled by inflow and outflow of $Na^+$, $Ca^{2+}$, $K^+$ in and out of the cells, and evaluating a membrane potential change caused by this inflow and outflow of the ions. On the other hand, the calcium imaging method is a method of staining cells using pigments (calcium fluorescent indicator) emitting fluorescence by bonding with calcium ions, and observing the fluorescence using a fluorescent microscope and the like.

CITATION LIST

Patent Literature

[PTL 1]
JP 2013-94168 A
[PTL 2]
JP 2013-21961 A

SUMMARY

According to some embodiments, a live cell analysis apparatus may comprise an electro stimulator arranged to apply first electrical stimulations to one or more live cells, and an image capture apparatus arranged to capture a sequence of images of the one or more live cells. The live cell analysis apparatus may further include at least one data processor configured to process the sequence of images to determine motion of the one or more live cells that is responsive to the applied first electrical stimulations.

In some embodiments, a method for analyzing live cells comprises acts of applying first electrical stimulations to one or more live cells, capturing a sequence of images, with an image capture apparatus, of the one or more live cells, and determining from the sequence of images, by at least one data processor, motion of the one or more live cells that is responsive to the applied first electrical stimulations.

According to some embodiments, a system for analyzing live cells comprises an electro stimulator arranged to apply first electrical stimulations to one or more live cardiomyocytes, and an image capture apparatus arranged to capture a sequence of images of the live cardiomyocytes. The system may further comprise data analysis apparatus connected to the image capture apparatus and configured to process the sequence of images to determine motion of the one or more live cells that is responsive to the applied first electrical stimulations and to determine a refractory period of the live cardiomyocytes.

Some embodiments include non-transitory data storage medium storing machine-readable instructions that, when executed on at least one data processor of a live cell analysis apparatus, cause the live cell analysis apparatus to: apply electrical stimulations to one or more live cardiomyocytes, capture a sequence of images, with an image capture apparatus, of the one or more live cardiomyocytes, determine from the sequence of images, by at least one data processor, motion of the one or more live cardiomyocytes that is responsive to the applied electrical stimulations, and calculate a refractory period for the one or more live cardiomyocytes based on the determined motion.

According to some embodiments, an apparatus for live cell analysis comprises an electro stimulation controller configured to control electrical stimulations applied to one or more live cells, an image processor configured to receive a sequence of images of the one or more live cells from an image capture apparatus, and at least one data processor that is configured to process the sequence of images to determine motion of the one or more live cells, wherein the motion is responsive to the applied electrical stimulations, and wherein the at least one data processor that is further configured to determine a refractory period for cardiomyocytes from the determined motion when the one or more live cells are cardiomyocytes.

Technical Problem

In the past, a QT interval of an electrocardiogram is used for the evaluation of the effect of a drug caused on cardiomyocytes. As a new index corresponding to this QT interval, a so-called "refractory period" attracts attention. The "refractory period" is a period in which a flow of $Na^+$ is suppressed for a certain period of time after the cardiomyocytes start contraction. However, currently, no method has yet been suggested by means of experiment.

In the MEA method explained above, the cardiomyocytes are evaluated using an index called FPD (field potential duration) as a value similar to a refractory period, but it is not clear whether this FPD value matches the refractory period. In the MEA method, the number of data depends on the number of electrodes, and a currently used apparatus having 64 electrodes (the maximum number of data is 64) has a difficulty in ensuring a sufficient number of data as the observation range becomes larger. Further, in the calcium imaging method, it is necessary to stain cells, and therefore, the calcium imaging method is not suitable for a long term measurement.

Therefore, it is a main object of the present disclosure is provide a cell evaluation apparatus, a cell evaluation method, a data analysis apparatus, and a data analysis method capable of deriving a refractory period of cardiomyocytes without staining.

Solution to Problem

A cell evaluation apparatus according to the present disclosure includes: an image-capturing unit configured to capture an image of motion of cardiomyocytes to which an electro stimulation has been applied; a motion amount calculation unit configured to calculate a motion amount of the cardiomyocytes corresponding to an electro stimulation application from image data captured by the image-capturing unit; and a refractory period calculation unit configured to calculate a refractory period of the cardiomyocytes on the basis of waveform information indicating time-change of the motion amount of the cardiomyocytes.

The apparatus may include an electro stimulation control unit configured to control an application condition of an electro stimulation given to the cardiomyocytes.

In that case, for example, the electro stimulation control unit applies a first electro stimulation for pacing excitability to any given position of the cardiomyocytes.

The electro stimulation control unit applies a first electro stimulation to the cardiomyocytes, and thereafter, may apply a second electro stimulation having any given phase difference from the first electro stimulation to a same or a different position as the first electro stimulation.

Further, the electro stimulation control unit can determine the phase difference between the first electro stimulation and the second electro stimulation on the basis of a time from when the cardiomyocytes start to contract in response to the first electro stimulation to a time when the cardiomyocytes attain a maximum relaxation.

Moreover, the electro stimulation control unit may apply an electro stimulation to the cardiomyocytes with changing a phase difference between the first electro stimulation and the second electro stimulation until the cardiomyocytes no longer react or until the cardiomyocytes react.

On the other hand, the refractory period calculation unit can calculate a refractory period of the cardiomyocytes, on the basis of two or more pieces of wave information having different phase differences between the first electro stimulation and the second electro stimulation.

The apparatus may further include a propagation characteristics calculation unit configured to calculate propagation characteristics of pulsation of the cardiomyocytes from motion amount data of the cardiomyocytes.

For example, the propagation characteristics is at least one of a propagation speed and a propagation direction.

A cell evaluation method according to the present disclosure includes: applying an electro stimulation to cardiomyocytes and thereby capturing an image of motion of the cardiomyocytes; calculating a motion amount of the cardiomyocytes corresponding to an electro stimulation application from captured image data; and calculating a refractory period of the cardiomyocytes on the basis of waveform information indicating time-change of the motion amount of the cardiomyocytes.

The cell evaluation method may further include calculating propagation characteristics of pulsation of the cardiomyocytes from motion amount data of the cardiomyocytes, and using the same image data to calculate the propagation characteristics and calculate the refractory period.

A data analysis apparatus according to the present disclosure includes: a motion amount calculation unit configured to calculate a motion amount of the cardiomyocytes corresponding to an electro stimulation application from image data of motion of cardiomyocytes to which an electro stimulation has been applied; and a refractory period calculation unit configured to calculate a refractory period of the cardiomyocytes on the basis of waveform information indicating time-change of the motion amount of the cardiomyocytes.

The apparatus may further include a propagation characteristics calculation unit configured to calculate propagation characteristics of pulsation of the cardiomyocytes from motion amount data of the cardiomyocytes.

A data analysis method according to the present disclosure includes: calculating a motion amount of the cardiomyocytes corresponding to an electro stimulation application from image data of motion of cardiomyocytes to which an electro stimulation has been applied; and calculating a refractory period of the cardiomyocytes on the basis of waveform information indicating time-change of the motion amount of the cardiomyocytes.

The data analysis method may further include calculating propagation characteristics of pulsation of the cardiomyocytes from motion amount data of the cardiomyocytes, and using the same image data to calculate the propagation characteristics and calculate the refractory period.

A cell evaluation system according to the present disclosure includes: an image-capturing apparatus configured to capture motion of cardiomyocytes to which an electro stimulation has been applied; and a data analysis apparatus including a motion amount calculation unit configured to calculate a motion amount of the cardiomyocytes corresponding to an electro stimulation application from image data captured by the image-capturing unit, and a refractory period calculation unit configured to calculate a refractory period of the cardiomyocytes on the basis of waveform information indicating time-change of the motion amount of the cardiomyocytes.

A program according to the present disclosure for causing a computer to achieve: a function of calculating a motion amount of the cardiomyocytes corresponding to an electro stimulation application from image data of motion of cardiomyocytes to which an electro stimulation has been applied; and a function of calculating a refractory period of the cardiomyocytes on the basis of waveform information indicating time-change of the motion amount of the cardiomyocytes.

Advantageous Effects of Invention

According to the present disclosure, a refractory period of cardiomyocytes, which is to be evaluated, can be derived without staining. It should be noted that the effects described here are not necessarily limited, and only any of the effects described in the present disclosure may be achieved.

BRIEF DESCRIPTION OF DRAWINGS

FIG. 1 is a figure illustrating an example of configuration of a cell evaluation apparatus according to a first embodiment of the present disclosure.

FIGS. 2A and 2B are schematic views illustrating examples of configurations of containers having electrodes.

FIG. 3 is a schematic view illustrating an electro stimulation application method in a case where a container not having any electrode is used.

FIG. 4 is a figure illustrating an example of configuration of a data analysis unit 3.

FIG. 5 is a block diagram illustrating an example of configuration of an electro stimulation application unit 4.

FIG. 6 is a flowchart diagram illustrating a method for measuring a refractory period of cardiomyocytes by using the cell evaluation apparatus 10 as shown in FIG. 1.

FIG. 7 is a figure illustrating a relationship between a time and a motion amount, which is motion amount data calculated by a data analysis unit.

FIGS. 8A to 8D are figures illustrating methods for applying electro stimulation.

FIG. 9A is motion amount data when the phase difference of electro stimulation S1-S2 is 335 milliseconds, and FIG. 9B is motion amount data when the phase difference is 340 milliseconds.

FIG. 10 is a figure illustrating application positions of electro stimulations S1, S2 on an isochron indication of propagation characteristics of the pulsation of cardiomyocytes which are to be evaluated.

FIG. 11A is motion amount data when the phase difference of electro stimulation S1-S2 is 370 milliseconds, and FIG. 11B is motion amount data when the phase difference is 380 milliseconds.

FIG. 12 is a figure illustrating application positions of electro stimulations S1, S2 on an isochron indication of propagation characteristics of the pulsation of cardiomyocytes which are to be evaluated.

FIG. 13A is motion amount data when the phase difference of electro stimulation S1-S2 is 390 milliseconds, and FIG. 13B is motion amount data when the phase difference is 395 milliseconds.

FIG. 14A is motion amount data when the phase difference of electro stimulations S1-S2 is 335 milliseconds, and FIG. 14B is motion amount data when the phase difference is 340 milliseconds.

FIG. 15 is a figure illustrating an estimation result of a point in time when passing a refractory period, which is shown on an isochron indication of propagation characteristics of the pulsation of cardiomyocytes which are to be evaluated.

FIG. 16 is a figure illustrating an example of configuration of a data analysis unit 30 of a cell evaluation apparatus according to a second embodiment of the present disclosure.

FIG. 17 is a flowchart illustrating a method using a cell evaluation apparatus according to the second embodiment of the present disclosure to simultaneously perform cardiomyocytes refractory period measurement and propagation characteristics measurement.

FIG. 18 is a figure illustrating a propagation speed calculation method.

FIG. 19 is a figure illustrating another propagation speed calculation method.

FIG. 20 is a figure illustrating another propagation speed calculation method.

FIG. 21 is a figure illustrating an estimation method for estimating an occurrence condition of spiral re-entry phenomenon.

FIG. 22 is a figure illustrating anisotropic excitability propagation.

FIG. 23 is a figure illustrating a schematic configuration of a cell evaluation system according to a third embodiment of the present disclosure.

DESCRIPTION OF EMBODIMENTS

Hereinafter, embodiments for carrying out the present disclosure will be explained in details with reference to attached drawings. It should be noted that the present disclosure is not limited to the embodiments shown below. The embodiments will be explained in the following order.
1. First embodiment (example of cell evaluation apparatus performing refractory period measurement of cardiomyocytes)
2. Second embodiment (example of cell evaluation apparatus for simultaneously performing refractory period measurement and propagation characteristics measurement of cardiomyocytes)
3. Third embodiment (example of cell evaluation system performing refractory period measurement of cardiomyocytes)

1. First Embodiment

Overall Configuration

First, a cell evaluation apparatus according to the first embodiment of the present disclosure will be explained. FIG. 1 is a figure illustrating an example of configuration of a cell evaluation apparatus according to the present embodiment. A cell evaluation apparatus 10 according to the present embodiment is configured to measure the refractory period of cardiomyocytes and evaluate the cardiomyocytes on the basis of the result, and as shown in FIG. 1, the cell evaluation apparatus 10 according to the present embodiment includes an image-capturing unit 1, an image data generation unit 2, a data analysis unit 3, an electro stimulation application unit 4, an evaluation unit 5, an indication unit 6, and the like. As described above, the "refractory period" is a period in which a flow of $Na^+$ is suppressed for a certain period of time after the cardiomyocytes start contraction. When a stimulation such as electricity is applied with an interval longer than the refractory period, $Na^+$ flows in and there is a response in the cardiomyocytes. On the other hand, when a stimulation such as electricity is applied with an interval shorter than the refractory period, Na channel is inactivated, and accordingly, inflow of $Na^+$ is suppressed, and there is no response in the cardiomyocytes. In an example of the present embodiment, electro stimulations are applied with multiple intervals, and presence/absence of response from the cardiomyocytes is analyzed from the change in the motion amount data, and the refractory period is calculated.

Evaluation Cell

Cells evaluated by the cell evaluation apparatus 10 according to the present embodiment may be those including cardiomyocytes including not only cardiomyocytes made by cell culturing technique, cardiomyocytes mass, cardiomyocytes sheet, and cardiac muscle tissue but also heart sections, and the like.

Image-Capturing Unit 1

The image-capturing unit 1 is configured to capture an image of a motion of cardiomyocytes to which electro stimulation has been applied, and the image-capturing unit 1 includes an image-capturing device 11, an object lens 12, a sample stage 13, an illumination light source 14, a container 15, and the like. FIG. 1 illustrates an example of configuration in a case where an image is captured using an inverted microscope, but the present disclosure is not limited thereto, and other types of microscopes such as a stereoscopic microscope and an upright microscope may also be used. Alternatively, without using a microscope, images may be captured by a camera including a lens and an image-capturing device.

On the other hand, the container 15 may be those capable of accommodating cardiomyocytes which are to be evaluated, and applying electro stimulation thereto. For example, a container having electrodes embedded with multiple microelectrodes may be used. FIGS. 2A and 2B are schematic views illustrating examples of configurations of containers having electrodes. The number of electrodes and the installation thereof in the container 15 are not particularly limited thereto. As shown in FIG. 2A, multiple electrodes 15a may be provided at an end portion with an interval therebetween, or as shown in FIG. 2B, a pair of electrodes 15a, 15b may be provided at any given position.

Further, the container 15 may be those without electrodes embedded therein. FIG. 3 is a schematic view illustrating an electro stimulation application method in a case where a container having no electrode is used. In this case, for example, as shown in FIG. 3, electro stimulation may be applied by bringing a pair of microelectrodes 41a, 41b into contact with any give portions of the cardiomyocytes 7 held in a culture fluid 8.

Image Data Generation Unit 2

The image data generation unit 2 generates evaluation-target image data on the basis of an image signal provided from the image-capturing unit 1, and records and saves the generated evaluation-target image data to, for example, an internal recording medium. The evaluation-target image data generated here is, for example, motion picture data obtained from a time when the electro stimulation is applied to a time when a certain period of time passes.

The image data generation unit 2 may extract only frame images in a limited period from multiple frame images provided from the image-capturing unit 1, and may generate evaluation-target image data. The image data generation unit 2 may extract, as a small frame image, a portion of the area of each frame image provided from the image-capturing unit 1, and make a motion picture including small frame images into evaluation-target image data.

Further, the image data generation unit 2 may apply any given image processing on each frame image provided from the image-capturing unit 1, and may make the image processing result thereof into evaluation-target image data. Examples of image processing include enlargement, reduction, rotation, deformation, correction of brightness and chromaticity, sharpness, noise reduction in images, intermediate frame image generation, and the like, but the image processing is not limited thereto. Various types of image processing can be applied.

Data Analysis Unit 3

FIG. 4 is a figure illustrating an example of configuration of the data analysis unit 3. The data analysis unit 3 is configured to detect motion of cardiomyocytes on the basis of the evaluation-target image data generated by the image data generation unit 2, and calculate an initial phase difference X (milliseconds) and a refractory period from the magnitude of the motion vector (motion amount). Then, as shown in FIG. 4, the data analysis unit 3 is provided with a motion detection unit 31, a motion amount calculation unit 32, a refractory period calculation unit 33, and the like.

The motion detection unit 31 performs motion detection on each block of the evaluation-target image data generated by the image data generation unit 2, and output the detection result (motion vector) to the motion amount calculation unit 32 as motion detection data. The motion detection method according to which the motion detection unit 31 detects the cardiomyocytes is not particularly limited, but, for example, it is possible to use a method of detecting how far any given point in an image has moved within a predetermined period of time by using block matching.

The motion amount calculation unit 32 calculates a motion amount on the basis of each piece of the motion detection data detected by the motion detection unit 31, and outputs the result to the electro stimulation application unit 4 or the refractory period calculation unit 33 as motion amount data. The motion amount calculation method of the motion amount calculation unit 32 is not particularly limited, but, for example, there is a method of dividing received motion detection data into new blocks, and calculating an average motion amount in each block.

The refractory period calculation unit 33 is configured to derive the refractory period of the evaluation-target cardiomyocytes from the motion amount data calculated by the motion amount calculation unit 32. The result calculated by the refractory period calculation unit 33 is output, as the refractory period data, to an evaluation unit 5, an indication unit 6, a printer (not shown), a storage unit (not shown), and the like.

Electro Stimulation Application Unit 4

FIG. 5 is a figure illustrating an example of configuration of the electro stimulation application unit 4. The electro stimulation application unit 4 is configured to apply electro stimulation to the evaluation-target cardiomyocytes, and as shown in FIG. 5, the electro stimulation application unit 4 includes a phase difference determination unit 42, an electro stimulation control unit 43, a power supply 44 and electrode 41, and the like. In this case, the electrode 41 may be anything capable of applying electro stimulation to the cardiomyocytes, and may be microelectrodes 15a, 15b embedded in the container 15, microelectrodes 41a, 41b provided separately from the container 15, and the like.

The phase difference determination unit 42 is configured to detect the initial phase difference X and the phase difference of two types of electro stimulations S1, S2 applied to the cardiomyocytes, on the basis of the received motion amount data. The result (phase difference) determined by the phase difference determination unit 42 is output to the electro stimulation control unit 43. In the normal state, the refractory period indicates a value close to the phase difference from the start of contraction to the maximum relaxation, and therefore, the initial phase difference X may be, for example, the phase difference from the start of contraction of the evaluation-target cardiomyocytes to the maximum relaxation (milliseconds), and in this case, it is not necessary to exhaustively allocate the stimulation phase differences, and the refractory period can be detected in a shorter time.

The electro stimulation control unit 43 is configured to control the condition of the electro stimulation applied to the cardiomyocytes accommodated in the container 15 on the basis of the result determined by the phase difference determination unit (phase difference) and the like. Application conditions controlled by the electro stimulation control unit 43 include application positions, the number of application points, application time, voltage, and the like.

Evaluation Unit 5

The evaluation unit 5 is configured to evaluate cardiomyocytes on the basis of the refractory period calculated by the data analysis unit 3. The contents of the evaluation of cardiomyocytes evaluated by the evaluation unit 5 are not particularly limited, but, for example, estimation of a refractory period area, cardiotoxicity evaluation, evaluation of homogeneity of a sheet when the cardiomyocytes sheet is made, estimation of occurrence conditions of the spiral re-entry phenomenon, and the like may be performed.

Indication Unit 6

The indication unit 6 is configured to indicate refractory period data calculated by the refractory period calculation unit 33, information related thereto, and the evaluation result made by the evaluation unit 5.

Operation

Subsequently, operation of the cell evaluation apparatus 10 of the present embodiment will be explained. More specifically, a method of measuring the refractory period of cardiomyocytes using the cell evaluation apparatus 10 will be explained. FIG. 6 is a flowchart diagram illustrating a method of evaluating the refractory period of cardiomyocytes using the cell evaluation apparatus 10. As shown in FIG. 6, when the cell evaluation apparatus 10 measures the refractory period of cardiomyocytes, the container 15 containing cardiomyocytes, a heart section, and the like which are to be evaluated is placed on the sample stage 13 of the image-capturing unit 1.

Then, the electro stimulation application unit 4 applies a pacing electro stimulation S1 to any given position of the cardiomyocytes, and the image-capturing unit 1 captures an image of motion of cardiomyocytes caused by the electro stimulation S1, and the image data generation unit 2 generates image data. The data analysis unit 3 using the image data analyzes pulsation of cardiomyocytes, and on the basis of the obtained motion amount data, the electro stimulation application unit 4 determines the initial phase difference X (milliseconds).

FIG. 7 is a figure illustrating a relationship between a time and a motion amount, which is motion amount data calculated by a data analysis unit. The motion amount data as shown in FIG. 7 indicate a movement amount with respect to the time, which is calculated by block matching processing for detecting how far any given point in the image described above moves within a predetermined period of time. The initial phase difference X can be calculated from, for example, the difference between the relaxation peak time and the time of the start of contraction as shown in FIG. 7.

Subsequently, the electro stimulation application unit 4 applies the pacing electro stimulation S1 from any given position once or multiple times, and thereafter, applies an electro stimulation S2 having the same phase difference as the initial phase difference X, and according to the same method as the method described above, the data analysis unit 3 analyzes the pulsation of the cardiomyocytes. More specifically, by using the image captured by the image-capturing unit 1 and generated by the image data generation unit 2, the data analysis unit 3 calculates the motion amount of the cardiomyocytes.

FIGS. 8A to 8D are figures illustrating an application position and an application method of electro stimulation. The electro stimulations S1, S2 may be applied to the same portion as shown in FIG. 8A, or may be applied from different positions as shown in FIG. 8B. Alternatively, the electro stimulations S1, S2 may be applied to multiple positions, and in such case, multiple electro stimulations S1, S2 may be applied to the same portion as shown in FIG. 8C, but the electro stimulation S2 may be applied to multiple portions different from the electro stimulation S1 as shown in FIG. 8D.

When the cardiomyocytes are determined to react in response to the electro stimulation S2 as a result of pulsation analysis, the electro stimulation application unit 4 applies the electro stimulation S1 again once or multiple times, and thereafter, the electro stimulation application unit 4 applies the electro stimulation S2 having a phase difference of (X−10) milliseconds, and the data analysis unit 3 analyzes the pulsation of the cardiomyocytes. The application of the electro stimulation S2 and the pulsation analysis are done upon changing the phase difference until the cardiomyocytes no longer react to the electro stimulation S2, and the cell refractory phase difference $Y_1$ (milliseconds) at which the cardiomyocytes no longer react is derived.

On the other hand, when the cardiomyocytes do not react to the electro stimulation S2, the electro stimulation application unit 4 applies the electro stimulation S1 again once or multiple times, and thereafter, the electro stimulation application unit 4 applies the electro stimulation S2 having a phase difference of (X+10) milliseconds, and the data analysis unit 3 analyzes the pulsation of the cardiomyocytes. The application of the electro stimulation S2 and the pulsation analysis are done upon changing the phase difference until the cells react to the electro stimulation S2, and the cell reaction phase difference $Y_2$ (milliseconds) at which the cardiomyocytes react is derived. In this case, the presence or absence of the reaction of the cardiomyocytes can be automatically determined by analyzing the motion amount data of the cardiomyocytes. For example, the correlation of the waveforms before and after the electro stimulation is derived, and when the correlation is high, the cardiomyocytes are determined not to have reacted, and when the correlation is low, the cardiomyocytes are determined to have reacted.

Thereafter, the refractory period calculation unit 33 calculates the refractory period of the evaluation-target cardiomyocytes from the cell refractory phase difference $Y_1$ (milliseconds) and cell reaction phase difference $Y_2$ (milliseconds) described above. FIG. 9A is motion amount data in a case where the phase difference of the electro stimulations S1-S2 is 335 milliseconds. FIG. 9B is motion amount data in a case where the phase difference is 340 milliseconds. As shown in FIG. 9A, in the pulsation analysis result in a case where the phase difference of the electro stimulations S1-S2 is configured to be 335 milliseconds, there seem to be no reaction of the cardiomyocytes caused by the electro stimulation S2.

In contrast, in the pulsation analysis result in a case where the phase difference of the electro stimulations S1-S2 as shown in FIG. 9B is 340 milliseconds, there seem to exist a reaction of the cardiomyocytes caused by the electro stimulation S2. Therefore, for this cardiomyocytes, the cell refractory phase difference $Y_1$ is calculated as 335 milliseconds, and the cell reaction phase difference $Y_2$ is calculated as 340 milliseconds. Then, the refractory period of the cardiomyocytes is derived as 335 to 340 ms from these calculation results. The refractory period data calculated according to the above method is indicated by the indication unit 6, and is used for evaluation of the homogeneity of the cardiomyocytes, the cardiotoxicity evaluation, and the like. For example, when the homogeneity of a cardiomyocytes sheet is evaluated, the refractory period measurement is performed upon changing the electro stimulation application position within the same cardiomyocytes sheet, and the position information as well as the refractory period data are indicated, so that the homogeneity can be indicated in a visualized manner. When cardiotoxicity caused by drug administration is evaluated, the refractory period data are compared between cardiomyocytes with drug administration and cardiomyocytes without drug administration, so that the refractory period elongation caused by drug administration can be evaluated in a quantitative manner.

The refractory period data calculated according to the above method may be indicated on the indication unit 6, or may be output to the evaluation unit 5 to be used to evaluate the cardiomyocytes. For example, when the cardiomyocytes are cultured in a mono layer manner, the cardiomyocytes may partially include cells which do not perform excitability propagation, and there may be variation in the refractory period within the sheet. Therefore, the refractory period measurement may be performed upon changing the electro stimulation application position within the same cardiomyocytes sheet, so that the variation in the refractory period within the cardiomyocytes sheet can be evaluated.

FIGS. 10 and 12 are figures illustrating the application positions of the electro stimulation S1, S2 shown on an isochron indication of propagation characteristics of pulsation of evaluation-target cardiomyocytes. FIGS. 11A and 11B are figures illustrating pulsation analysis results when an electro stimulation is applied to the positions as shown in FIG. 10, and FIGS. 13A and 13B are figures illustrating pulsation analysis result when an electro stimulation is applied to the positions as shown in FIG. 12.

In the isochron indication as shown in FIGS. 10 and 12, a rising time of each waveform in the waveform information is identified, and waveforms of which differences are within a predetermined range are made into an equal time block, and each of the equal time blocks is indicated in the same color. In FIGS. 10 and 12, a block in which the rising time is earlier is indicated in a darker color, and as the rising time is at a later point in time, the block is indicated in a lighter color. The isochron indication allows easy understanding of how the pulsation propagations in the cardiomyocytes sheet. This isochron indication can be obtained for each pulsation, and therefore, the stability of the pulsation can be evaluated in more details.

For example, the equal time line shown in FIG. 10 indicates that it takes 6 milliseconds for the excitability caused by the electro stimulation S1 applied to the point A to reach the application position of the electro stimulation S2 (point B). As shown in FIG. 11A, when the phase difference of the electro stimulation S1-S2 is 370 milliseconds, the pulsation analysis result shows no reaction of cardiomyocytes caused by the electro stimulation S2. On the other hand, as shown in FIG. 11B, when the phase difference of the electro stimulation S1-S2 is 380 milliseconds, the pulsation analysis result shows a reaction of cardiomyocytes caused by the electro stimulation S2.

Therefore, in this cardiomyocytes sheet, the cell refractory phase difference $Y_1$ is calculated as 370 milliseconds, and the cell reaction phase difference $Y_2$ is calculated as 380 milliseconds. The refractory period is in a range equal to or more than (cell reaction phase difference $Y_1$—a time it takes for the propagation to travel from S1 to S2), and equal to or less than (cell reaction phase difference $Y_2$—time it takes for the propagation to travel from S1 to S2), and therefore, it is derived as 365 to 375 ms.

On the other hand, from the equal time lines shown in FIG. 12, it is understood that a time it takes for the excitability caused by the electro stimulation S1 applied to the point C to reach the application position of the electro stimulation S2 (point D) is 6 milliseconds. As shown in FIG. 13A, when the phase difference of the electro stimulation S1-S2 is 390 milliseconds, the pulsation analysis result shows no reaction of cardiomyocytes caused by the electro stimulation S2. On the other hand, as shown in FIG. 13B, when the phase difference of the electro stimulation S1-S2 is 395 milliseconds, the pulsation analysis result shows a reaction of cardiomyocytes caused by the electro stimulation S2.

Therefore, in this cardiomyocytes sheet, the cell refractory phase difference $Y_1$ is calculated as 390 milliseconds, and the cell reaction phase difference $Y_2$ is calculated as 395 milliseconds, and the refractory period of the cardiomyocytes at the point D is derived as 384 to 389 ms. The distance between the point B and the point D on the evaluation-target cardiomyocytes sheet is 900 micrometers. According to the above result, it is confirmed that there is variation in the refractory period in this cardiomyocytes sheet.

When the refractory period measurement result is used, it is possible to estimate whether which area is theoretically in the refractory period after the electro stimulation S1 is applied, and at which point in time the cardiomyocytes accept external stimulation after the electro stimulation S1 is applied. FIG. 14A is motion amount data when the phase difference of the electro stimulation S1-S2 is 335 milliseconds, and FIG. 14B is motion amount data when the phase difference is 340 milliseconds. From the result shown in FIGS. 14A and 14B, it is understood that the refractory period of the evaluation-target cardiomyocytes is 335 to 340 milliseconds.

FIG. 15 is a figure illustrating an estimation result of a point in time when passing a refractory period of the pulsation of the evaluation-target cardiomyocytes. From the equal time line evaluation result shown in FIG. 15, a time it takes for the propagation to travel from the application position of the electro stimulation S1 to each point of the points A to E is as follows: the time to the point A is derived as 25 milliseconds, the time to the point B is derived as 20 milliseconds, the time to the point C is derived as 15 milliseconds, the time to the point D is derived as 20 milliseconds, and the time to the point E is derived as 25 milliseconds. The above result indicates that when, for the electro stimulation S1 at each of the points A to E, the electro stimulation S2 is applied with a phase difference of 360 to 365 milliseconds at the point A, a phase difference of 355 to 360 milliseconds at the point B, a phase difference of 350 to 355 milliseconds at the point C, a phase difference of 355 to 360 milliseconds at the point D, and a phase difference of 360 to 365 milliseconds at the point E, the cell at each point is estimated as being in the refractory period. On the basis of the estimation values, the electro stimulation S2 is actually applied at each point, so that the variation of the refractory period in the cardiomyocytes sheet can be evaluated.

The step of calculating the motion amount of the cardiomyocytes described above and the step of calculating the refractory period of the cardiomyocytes can be implemented by making a computer program for realizing each function of an information processing apparatus and implementing the computer program on a personal computer and the like. Such computer program may be stored to, for example, a recording medium such as a magnetic disk, an optical disk, a magneto-optical disk, and a flash memory, or distributed via a network.

As described in details, the cell evaluation apparatus according to the present embodiment uses the motion vector analysis and the like, and can derive the refractory period of the cardiomyocytes without staining. Therefore, the effect and the safety in the development of new pharmaceuticals and model tests of cardiac diseases can be evaluated in a simpler manner and with a higher degree of accuracy than in the past. The variation in the refractory period in the cardiomyocytes sheet is adopted as an index, so that the uniformity of the cardiomyocytes can be evaluated. Further, the cell evaluation apparatus according to the present embodiment can evaluate the cardiomyocytes over a long period of time.

2. Second Embodiment

Overall Configuration

Subsequently, a cell evaluation apparatus according to a second embodiment of the present disclosure will be explained. In recent years, in arrhythmogenic evaluation, it is suggested that evaluation with only QT elongation is insufficient, and in particular, it is known that propagation abnormality of an electric signal between the cardiomyocytes (propagation speed, propagation direction) occurs when critical symptoms such as ventricular fibrillation occurs in particular. For this reason, a technique for evaluating the propagation abnormality of the cardiomyocytes at the same time as the refractory period measurement as described above has not yet been reported. Therefore, the inventor of the present application uses a motion detection technique using motion vector analysis, and can perform the propagation evaluation and the refractory period measurement of the cardiomyocytes at the same time.

More specifically, in the cell evaluation apparatus according to the present embodiment, the data analysis unit performs the refractory period calculation and the propagation characteristics calculation of the evaluation-target cardiomyocytes at the same time. FIG. 16 is a block diagram illustrating an example of configuration of the data analysis unit 30 of the cell evaluation apparatus according to the present embodiment. FIG. 17 is a flowchart illustrating a method according to which the cell evaluation apparatus according to the present embodiment is used to perform the refractory period measurement and the propagation characteristics measurement of the cardiomyocytes at the same time. In FIG. 16, the same constituent elements as those of the data analysis unit 3 shown in FIG. 4 are denoted with the same reference numerals, and detailed description thereabout is omitted.

Data Analysis Unit 30

As shown in FIG. 16, the cell evaluation apparatus according to the present embodiment, the data analysis unit 30 is provided with a propagation characteristics calculation unit 34, and is configured to be able to calculate propagation characteristics such as the propagation speed and the propagation direction at the same time as the refractory period measurement. In the cell evaluation apparatus according to the present embodiment, the configuration other than the above is the same as the first embodiment explained above.

Operation

Subsequently, a method used by the cell evaluation apparatus according to the present embodiment to perform the refractory period measurement and the propagation characteristics measurement of the cardiomyocytes at the same time will be explained. When the cell evaluation apparatus according to the present embodiment measures the refractory period and propagation characteristics of the cardiomyocytes, the container 15 containing cardiomyocytes, a heart section, and the like which are to be evaluated is placed on the sample stage 13 of the image-capturing unit 1 like the first embodiment explained above.

Then, the electro stimulation application unit 4 applies a pacing electro stimulation S1 to any given position of the cardiomyocytes, and the image-capturing unit 1 captures an image of motion of cardiomyocytes caused by the electro stimulation S1, and the image data generation unit 2 generates image data. Using the image data, the data analysis unit 30 analyzes the pulsation of the cardiomyocytes, and on the basis of the obtained motion amount data, the propagation speed of the excitability is calculated, and the electro stimulation application unit 4 determines the initial phase difference X (milliseconds).

FIGS. 18 to 20 are figures illustrating a propagation speed calculation method. The calculation method of the propagation speed is not particularly limited, and may be global conduction velocity, local conduction velocity, mean conduction velocity, and the like. As shown in FIG. 18, the global conduction velocity is a method of dividing image data into any given size, finding the place where the excitability is finally transmitted in the cell sheet, measuring the time it takes for the excitability to travel to the location, and calculating the speed.

As shown in FIG. 19, the local conduction velocity is a method of dividing image data into any given size, selecting any given position, measuring a time it takes for the excitability to propagate to each location, and calculating a speed Vi (=distance/propagation time). As shown in FIG. 19, the mean conduction velocity is a method of dividing image data into any given size and extracting points at an equal distance from a stimulation application position, then deriving propagation speeds $V_1$ to $V_8$ at which the excitability propagates to each position, and deriving the average value and the standard deviation thereof.

Among these calculation methods, in particular, the mean conduction velocity is preferable, because evaluation is performed in view of the variation in the propagation speeds, which enables evaluating the anisotropy of propagation.

Subsequently, the electro stimulation application unit 4 applies a pacing electro stimulation S1 from any given position once or multiple times, and thereafter, applies an electro stimulation S2 having the same phase difference as the initial phase difference X, and according to the same method as the method described above, the data analysis unit 30 analyzes the pulsation of the cardiomyocytes according to the same method as the method described above. More specifically, the image-capturing unit 1 captures an image, and by using the image generated by the image data generation unit 2, the data analysis unit 30 calculates the motion amount of the cardiomyocytes.

When the cardiomyocytes are determined to react in response to the electro stimulation S2 as a result of pulsation analysis, the electro stimulation application unit 4 applies the electro stimulation S1 again once or multiple times, and thereafter, the electro stimulation application unit 4 applies the electro stimulation S2 having a phase difference of (X−10) milliseconds, and the data analysis unit 30 analyzes the pulsation of the cardiomyocytes. The application of the electro stimulation S2 and the pulsation analysis are done upon changing the phase difference until the cardiomyocytes no longer react to the electro stimulation S2, and the cell refractory phase difference $Y_1$ (milliseconds) at which the cardiomyocytes no longer react is derived.

On the other hand, when the cardiomyocytes do not react to the electro stimulation S2, the electro stimulation application unit 4 applies the electro stimulation S1 again once or multiple times, and thereafter, the electro stimulation application unit 4 applies the electro stimulation S2 having a phase difference of (X+10) milliseconds, and the data analysis unit 30 analyzes the pulsation of the cardiomyocytes. The application of the electro stimulation S2 and the pulsation analysis are done upon changing the phase difference until the cells react to the electro stimulation S2, and the cell reaction phase difference $Y_2$ (milliseconds) at which the cardiomyocytes react is derived.

Thereafter, the refractory period calculation unit 33 calculates the refractory period of the evaluation-target cardiomyocytes from the cell refractory phase difference $Y_1$ (milliseconds) and cell reaction phase difference $Y_2$ (milliseconds) described above. The refractory period data and the propagation characteristics data calculated according to the above method may be indicated on the indication unit 6, or may be output to the evaluation unit 5 to be used to evaluate the cardiomyocytes.

The cell evaluation apparatus according to the present embodiment uses the data and can evaluate the propagation speed, the propagation direction, and the refractory period, and therefore, the cell evaluation apparatus according to the present embodiment is particularly effective for the safety test of drugs such as cardiotoxicity test. In addition, the cell evaluation apparatus according to the present embodiment can also be applied to occurrence condition estimation of spiral re-entry which is known as a cause of lethal ventricular fibrillation.

In this case, the cause of spiral re-entry is considered to be as follows.
(1) When cells in a portion where the cardiomyocytes sheet exists are out of the refractory period, an external stimulation is applied at that point.
(2) The excitability propagates to only a portion which is out of the refractory period, so that anisotropic excitability propagation occurs.
(3) The excitability propagation successively propagates to the cells which are out of the refractory period, and therefore, when the propagation speed satisfies a certain condition, the excitability propagation perpetually continues.

As can be seen from the above, it is understood that occurrence of anisotropic excitability propagation is important in the stage of occurrence of spiral re-entry.

FIG. 21 is a figure illustrating an occurrence condition estimation method of spiral re-entry phenomenon. FIG. 22 is a figure illustrating anisotropic excitability propagation. For example, when the estimation result of the refractory period area as shown in FIG. 21 is used and the electro stimulation S2 is applied before the entire cardiomyocytes sheet is out of the refractory period, the anisotropic excitability propagation can be caused. Then, whether the spiral entry occurs or not can be predicted by evaluating the propagation speed of the anisotropic excitability propagation.

More specifically, when the electro stimulation S2 was applied to the cardiomyocytes sheet shown in FIG. 21 at the position (point E) where the phase difference from the electro stimulation S1 is 360 milliseconds, the anisotropic excitability propagation shown in FIG. 22 was found. In this evaluation, a time it took for the excitability caused by the electro stimulation S2 to return back to the position (point E) where the electro stimulation S2 had been applied was 35 milliseconds, and the refractory period of the cell was 335 to 340 milliseconds, and therefore, the spiral re-entry did not occur. However, when the propagation speed significantly drops and the refractory period is reduced because of some reason, it may be possible that the spiral re-entry occur.

As described above, by using the cell evaluation apparatus according to the present embodiment, the propagation speed, the propagation direction, and the refractory period can be evaluated at the same time, and a dangerous external stimulation can be predicted, and drug evaluation under the stimulation condition can be performed. In the cell evaluation apparatus according to the present embodiment, the configuration other than the above is the same as the first embodiment explained above.

The cell evaluation apparatus according to the first and second embodiments explained above perform application of electro stimulation and pulsation analysis in a series of operations, but the present disclosure is not limited thereto. For example, the electro stimulation is applied by changing the condition in advance, and the result thereof is stored to a storage unit of the apparatus or a storage medium separately provided. Then, the data analysis unit in the apparatus or a data analysis apparatus which is different from the measurement apparatus analyzes image data, calculates the refractory period of the cardiomyocytes, and calculates the propagation speed and the propagation direction, and can also evaluate them.

3. Third Embodiment

Subsequently, a cell evaluation system according to the third embodiment of the present disclosure will be explained. FIG. 23 is a figure illustrating a schematic configuration of a cell evaluation system according to the present embodiment. As shown in FIG. 23, the cell evaluation system according to the present embodiment includes an image-capturing apparatus 50 configured to capture images of motion of cardiomyocytes to which an electro stimulation has been applied, and a data analysis apparatus including a motion amount calculation unit and a refractory period calculation unit. Further, the cell evaluation system according to the present embodiment may be connected to a server, a display apparatus, and the like.
Image-Capturing Apparatus 50

The image-capturing apparatus 50 may be any apparatus capable of capturing the images of the motion of the cardiomyocytes to which an electro stimulation has been applied, and may be various kinds of microscopes and a camera having an image-capturing device.

The container and the like may be configured in the same manner as the first embodiment explained above.
Data Analysis Apparatus 60

The data analysis apparatus includes a motion amount calculation unit configured to calculate the motion amount of the cardiomyocytes corresponding to the electro stimulation application from the image data captured by the image-capturing apparatus 50 and a refractory period calculation unit configured to calculate the refractory period of the cardiomyocytes on the basis of waveform information indicating time-change in the motion amount of the cardiomyocytes. The configuration other than the above is the same as those of the first and second embodiments explained above.
Server The server is connected via a network to an image-capturing apparatus 50, a data analysis apparatus 60, a display apparatus, and the like, and is provided with an information storage unit and the like. The server manages various kinds of data uploaded from the image-capturing apparatus 50 and the data analysis apparatus 60, and outputs the data to the display apparatus and the data analysis apparatus 60 upon request.
Display Apparatus The display apparatus displays data of electric characteristics measured by the image-capturing apparatus 50 and various kinds of data and the like calculated by the data analysis apparatus 60. It should be noted that the display apparatus may be provided with an information input unit for allowing a user to select and input displayed data. In this case, the information which is input by the user is transmitted via the network to the server and the data analysis apparatus 60.

The cell evaluation system according to the present embodiment can also evaluate the propagation speed, the propagation direction, and the refractory period at the same time, and can predict dangerous external stimulation, and can derive the refractory period of the evaluation-target cardiomyocytes without staining. In cell evaluation system according to the present embodiment, the configuration and advantages other than the above are the same as those of the first embodiment and the second embodiment.

The present disclosure may also be configured as follows.

(1)
A live cell analysis apparatus that comprises an electro stimulator arranged to apply first electrical stimulations to one or more live cells, an image capture apparatus arranged to capture a sequence of images of the one or more live cells, and at least one data processor configured to process the sequence of images to determine motion of the one or more live cells that is responsive to the applied first electrical stimulations.

(2)
The apparatus according to (1), wherein the at least one processor is further configured to determine a refractory period for cardiomyocytes from the determined motion when the one or more live cells are cardiomyocytes.

(3)
The apparatus according to (1) or (2), wherein the electro stimulator is configured to apply the first electrical stimulations for pacing cardiomyocytes, and the at least one data processor is further configured to process a sequence of images of the cardiomyocytes to determine a first phase delay between an initial contraction of the cardiomyocytes and a relaxation time of the cardiomyocytes.

(4)
The apparatus according to (3), wherein the electro stimulator is configured to apply second electrical stimulations at a second time that is delayed from the first electrical stimulations by a selectively varied second phase delay.

(5)
The apparatus according to (4), wherein the second phase delay is initially set to be equivalent to the first phase delay.

(6)
The apparatus according to (4) or (5), wherein the at least one processor is further configured to determine a refractory period for the cardiomyocytes from at least the determined motion and a value of the second phase delay.

(7)
A method for analyzing live cells comprising acts of applying first electrical stimulations to one or more live cells, capturing a sequence of images, with an image capture apparatus, of the one or more live cells, and determining from the sequence of images, by at least one data processor, motion of the one or more live cells that is responsive to the applied first electrical stimulations.

(8)
The method according to (7), further comprising determining a refractory period for cardiomyocytes from the determined motion when the one or more live cells are cardiomyocytes.

(9)
The method according to (8), further comprising determining a first refractory period for first cardiomyocytes from first determined motion data when the first cardiomyocytes are not treated with a pharmaceutical drug, determining a second refractory period for second cardiomyocytes from second determined motion data when the second cardiomyocytes are treated with a pharmaceutical drug, and comparing the first refractory period and the second refractory period.

(10)
The method according to any one of (7) through (9), further comprising applying the first electrical stimulations for pacing cardiomyocytes and determining, by the at least one data processor, a first phase delay between an initial contraction of the cardiomyocytes and a relaxation time of the cardiomyocytes.

(11)
The method according to (10), further comprising applying second electrical stimulations at a second time that is delayed from the first electrical stimulations by a selectively varied second phase delay.

(12)
The method according to (11), further comprising initially setting the second phase delay to be equivalent to the first phase delay.

(13)
The method according to (11) or (12), further comprising calculating a refractory period for the cardiomyocytes from at least the determined motion and a value of the second phase delay.

(14)
The method according to any one of (8) through (13), wherein calculating the refractory period comprises producing at least one waveform representative of the determined motion, and analyzing the at least one waveform to calculate the refractory period.

(15)
The method according to any of (11) through (14), wherein calculating the refractory period comprises changing the second phase delay until the cardiomyocytes no longer respond to the second electrical stimulations and/or until the cardiomyocytes respond to the second electrical stimulations.

(16)
The method according to any of (8) through (15), further comprising determining a propagation speed and/or a propagation direction from the determined motion of the cardiomyocytes.

(17)
The method according to (16), wherein the propagation speed and/or the propagation direction and the refractory period are determined from the same sequence of images.

(18)
The method according to any one of (8) through (17), further comprising changing a position of at least the first electrical stimulations to one or more positions, determining refractory periods corresponding to the one or more positions, and determining a homogeneity in response of the cardiomyocytes from the determined refractory periods associated with the one or more positions.

(19)
A system for analyzing live cells comprising an electro stimulator arranged to apply first electrical stimulations to one or more live cardiomyocytes, an image capture apparatus arranged to capture a sequence of images of the live cardiomyocytes, and data analysis apparatus connected to the image capture apparatus and configured to process the sequence of images to determine motion of the one or more live cells that is responsive to the applied first electrical stimulations and to determine a refractory period of the live cardiomyocytes.

(20)

Non-transitory data storage medium storing machine-readable instructions that, when executed on at least one data processor of a live cell analysis apparatus, cause the live cell analysis apparatus to apply electrical stimulations to one or more live cardiomyocytes, capture a sequence of images, with an image capture apparatus, of the one or more live cardiomyocytes, determine from the sequence of images, by at least one data processor, motion of the one or more live cardiomyocytes that is responsive to the applied electrical stimulations, and calculate a refractory period for the one or more live cardiomyocytes based on the determined motion.

(21)

An apparatus for live cell analysis comprising an electro stimulation controller configured to control electrical stimulations applied to one or more live cells, an image processor configured to receive a sequence of images of the one or more live cells from an image capture apparatus, and at least one data processor that is configured to process the sequence of images to determine motion of the one or more live cells, wherein the motion is responsive to the applied electrical stimulations, and wherein the at least one data processor that is further configured to determine a refractory period for cardiomyocytes from the determined motion when the one or more live cells are cardiomyocytes.

The advantages described in this specification are merely an example, and the embodiments are not limited thereto, and may have other advantages.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

1 Image-capturing unit
2 Image data generation unit
3, 30 Data analysis unit
4 Electro stimulation application unit
5 Evaluation unit
6 Indication unit
7 Cardiomyocytes
8 Culture fluid
10 Cell evaluation apparatus
11 Image-capturing device
12 Object lens
13 Sample stage
14 Illumination light source
15 Container
15a, 15b, 41, 41a, 41b, Electrode
31 Motion detection unit
32 Motion amount calculation unit
33 Refractory period calculation unit
42 Phase difference determination unit
43 Electro stimulation control unit
44 Power supply
50 Image-capturing apparatus
60 Data analysis apparatus

The invention claimed is:

1. A live cell analysis apparatus, comprising:
an electro stimulator configured to apply first electrical stimulations to at least one live cell;
a microscope configured to capture a sequence of images of the at least one live cell; and
at least one data processor configured to:
process the sequence of images to determine motion of the at least one live cell that is responsive to the applied first electrical stimulations; and
determine a refractory period for the at least one live cell based on the determined motion.

2. The live cell analysis apparatus of claim 1, wherein the at least one live cell corresponds to at least one cardiomyocyte.

3. The live cell analysis apparatus of claim 1, wherein:
the electro stimulator is further configured to apply the first electrical stimulations for pacing a plurality of cardiomyocytes, and
the at least one data processor is further configured to process the sequence of images of the plurality of cardiomyocytes to determine a first phase delay between an initial contraction of the plurality of cardiomyocytes and a relaxation of the plurality of cardiomyocytes.

4. The live cell analysis apparatus of claim 3, wherein the electro stimulator is further configured to apply second electrical stimulations to the at least one live cell, delayed from the first electrical stimulations by a selectively varied second phase delay.

5. The live cell analysis apparatus of claim 4, wherein the selectively varied second phase delay is initially set equivalent to the first phase delay.

6. The live cell analysis apparatus of claim 4, wherein the at least one data processor is further configured to determine a refractory period for the plurality of cardiomyocytes based on at least the determined motion and a value of the selectively varied second phase delay, and wherein the plurality of cardiomyocytes comprise the at least one live cell.

7. A method for analyzing live cells, the method comprising:
applying first electrical stimulations to at least one live cell;
capturing a sequence of images, with a microscope, of the at least one live cell;
determining by at least one data processor:
motion of the at least one live cell based on the sequence of images, wherein the motion is based on the applied first electrical stimulations; and
a refractory period for at least one live cell based on the determined motion.

8. The method of claim 7, wherein the at least one live cell correspond to at least one cardiomyocyte.

9. The method of claim 8, further comprising:
determining a first refractory period for a plurality of first cardiomyocytes of the plurality of cardiomyocytes based on first determined motion data, wherein the plurality of first cardiomyocytes are not treated with a pharmaceutical drug;
determining a second refractory period for a plurality of second cardiomyocytes of the plurality of cardiomyocytes based on second determined motion data, wherein the plurality of second cardiomyocytes are treated with the pharmaceutical drug; and
comparing the first refractory period and the second refractory period.

10. The method of claim 7, further comprising:
applying the first electrical stimulations for pacing a plurality of cardiomyocytes; and
determining, by the at least one data processor, a first phase delay between an initial contraction of the plurality of cardiomyocytes and a relaxation of the plurality of cardiomyocytes.

11. The method of claim 10, further comprising applying second electrical stimulations to the at least one live cell, delayed from the first electrical stimulations by a selectively varied second phase delay.

12. The method of claim 11, further comprising initially setting the selectively varied second phase delay equivalent to the first phase delay.

13. The method of claim 11, further comprising calculating a refractory period for the plurality of cardiomyocytes based on at least the determined motion and a value of the selectively varied second phase delay, wherein the plurality of cardiomyocytes comprise the at least one live cell.

14. The method of claim 13, wherein calculating the refractory period comprises:
producing at least one waveform representative of the determined motion; and
analyzing the at least one waveform to calculate the refractory period.

15. The method of claim 13, wherein calculating the refractory period for the plurality of cardiomyocytes comprises changing the selectively varied second phase delay until one of:
the plurality of cardiomyocytes no longer respond to the second electrical stimulations, or
the plurality of cardiomyocytes respond to the second electrical stimulations.

16. The method of claim 13, further comprising determining one of a propagation speed or a propagation direction based on the determined motion.

17. The method of claim 16, wherein one of the propagation speed or the propagation direction, and the refractory period are determined from the sequence of images.

18. The method of claim 13, further comprising:
changing a first position of at least the first electrical stimulations to at least one second position;
determining a third refractory period corresponding to the at least one second position; and
determining a homogeneity in response of the plurality of cardiomyocytes from the determined third refractory period associated with the at least one second position.

19. A system to analyze live cells, the system comprising:
an electro stimulator configured to apply first electrical stimulations to at least one live cardiomyocyte;
a microscope configured to capture a sequence of images of the at least one live cardiomyocyte; and
at least one data processor connected to the microscope and the at least one data processor configured to:
process the sequence of images to determine motion of the at least one live cardiomyocyte, wherein the motion is based on the applied first electrical stimulations; and
determine a refractory period of the at least one live cardiomyocyte.

20. A non-transitory computer-readable medium having stored thereon computer-executable instructions that, when executed by at least one data processor of a live cell analysis apparatus, cause the live cell analysis apparatus to:
apply electrical stimulations to at least one live cardiomyocyte;
capture a sequence of images, with a microscope, of the at least one live cardiomyocyte;
determine from the sequence of images, by the at least one data processor, motion of the at least one live cardiomyocyte, wherein the motion is based on the applied electrical stimulations; and
calculate a refractory period for the at least one live cardiomyocyte based on the determined motion.

21. An apparatus for live cell analysis, comprising:
a controller configured to control electrical stimulations applied to at least one live cell;
an image processor configured to receive a sequence of images of the at least one live cell from a microscope; and
at least one data processor configured to:
process the sequence of images to determine motion of the at least one live cell, wherein the motion is based on the applied electrical stimulations, and
determine a refractory period for a plurality of cardiomyocytes based on the determined motion, wherein the at least one live cell is at least one cardiomyocyte of the plurality of cardiomyocytes.

* * * * *